United States Patent
Ishida

(10) Patent No.: US 9,745,583 B2
(45) Date of Patent: Aug. 29, 2017

(54) LIPOSOME FOR TOPICAL ADMINISTRATION AND APPLICATION THEREOF

(71) Applicant: DELTA-FLY PHARMA, INC., Tokuchima-shi, Tokushima (JP)

(72) Inventor: Tatsuhiro Ishida, Tokushima (JP)

(73) Assignee: DELTA-FLY PHARMA, INC., Tokushima-Shi (JP)

( * ) Notice: Subject to any disclaimer, the term of this patent is extended or adjusted under 35 U.S.C. 154(b) by 0 days.

(21) Appl. No.: 14/888,006

(22) PCT Filed: Nov. 1, 2013

(86) PCT No.: PCT/JP2013/080367
§ 371 (c)(1),
(2) Date: Oct. 29, 2015

(87) PCT Pub. No.: WO2014/178152
PCT Pub. Date: Nov. 6, 2014

(65) Prior Publication Data
US 2016/0208263 A1  Jul. 21, 2016

(30) Foreign Application Priority Data

Apr. 30, 2013 (JP) ................................. 2013-095950

(51) Int. Cl.
*A61K 9/127* (2006.01)
*C12N 15/113* (2010.01)
*A61K 31/519* (2006.01)
*A61K 31/7088* (2006.01)
*A61K 31/713* (2006.01)
*C12N 15/11* (2006.01)
*A61K 45/06* (2006.01)
*A61K 47/48* (2006.01)

(52) U.S. Cl.
CPC ........ *C12N 15/1137* (2013.01); *A61K 9/1271* (2013.01); *A61K 9/1272* (2013.01); *A61K 31/519* (2013.01); *A61K 31/7088* (2013.01); *A61K 31/713* (2013.01); *A61K 45/06* (2013.01); *A61K 47/48815* (2013.01); *C12N 15/111* (2013.01); *C12N 2310/14* (2013.01); *C12N 2310/531* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,744,159 A | 4/1998 | Yagi et al. | |
| 2002/0111326 A1 | 8/2002 | Tanaka et al. | |
| 2008/0306153 A1* | 12/2008 | Panzner | A61K 9/127 514/558 |
| 2010/0112042 A1 | 5/2010 | Polisky et al. | |
| 2011/0229581 A1 | 9/2011 | Zhao et al. | |
| 2012/0016012 A1 | 1/2012 | Wada et al. | |
| 2012/0301537 A1 | 11/2012 | Ishida et al. | |

FOREIGN PATENT DOCUMENTS

| | | |
|---|---|---|
| EP | 2 716 304 A1 | 4/2014 |
| JP | 9-248182 A | 9/1997 |
| JP | 2010-513354 A | 4/2010 |
| TW | 201021853 A1 | 6/2010 |
| TW | 201300113 A | 1/2013 |
| WO | WO 98/45463 A1 | 10/1998 |
| WO | WO 2005/067632 A2 | 7/2005 |
| WO | WO 2006/048329 A1 | 5/2006 |
| WO | WO 2008/074487 A1 | 5/2006 |
| WO | WO 2010/113844 A1 | 10/2010 |
| WO | WO 2012/161196 A1 | 11/2012 |
| WO | WO 2013/149140 A1 | 10/2013 |
| WO | WO 2013/177419 A2 | 11/2013 |

OTHER PUBLICATIONS

Kikuchi et al, Development of Novel Cationic Liposomes for Efficient Gene Transfer into Peritoneal Disseminated Tumor, 1999, Human Gene Therapy, 10: 947-955.*
European Journal of Cancer, 24th EORTC—NCI—AACR Symposium on Molecular Targets and Cancer Therapeutics, vol. 48, Supplement 6, Nov. 2012, pp. 69-70.
International Search Report issued in PCT/JP2013/080367, mailed on Jan. 7, 2014.
Ishida et al., "An entirely novel nanoparticle carrying a bioactive shRNA molecule (DFP-10825) could be clinically effective against the high risk patients with mesothelioma relapsed or refractory after treatment with pemetrexed based chemotherapy" 24th EORTC—NCI—AACR Symposium on Molecular Targets and Cancer Therapeutics, Nov. 7, 2012, 1 page.
Leng et al., "Advances in Systemic siRNA Delivery", Drugs Future., vol. 34, No. 9, Sep. 2009, 721, pp. 1-30.
Ozpolat et al., "Nanomedicine based approaches for the delivery of siRNA in cancer", Journal of Internal Medicine, vol. 267, 2009, pp. 44-53.
Written Opinion issued in PCT/JP2013/080367, mailed on Jan. 7, 2014.
Wu et al., "Lipidic Systems for in Vivo siRNA Delivery", The AAPS Journal, vol. 11, No. 4, Dec. 2009, pp. 639-652.
Candiani et al., "Bioreducible Liposomes for Gene Delivery: From the Formulation to the Mechanism of Action," PLoS ONE (Oct. 2010), vol. 5, No. 10, e 13430, pp. 1-8.
Nicol et al., "Effect of Phospholipid Composition on an Amphipathic Peptide-Mediated Pore Formation in Bilayer Vesicles," Biophysical Journal (Feb. 2000), vol. 78, pp. 818-829.

(Continued)

*Primary Examiner* — Kate Poliakova-Georgantas
(74) *Attorney, Agent, or Firm* — Birch, Stewart, Kolasch & Birch, LLP

(57) ABSTRACT

This invention provides a novel delivery means that enables efficient delivery of an active ingredient to a target cell. Such novel delivery means is a liposome for topical administration that consists of dioleylphosphatidylethanolamine (DOPE), phosphatidylcholine, and cationic lipid, that is not modified with PEG, and that is free of cholesterol.

15 Claims, 18 Drawing Sheets
(6 of 18 Drawing Sheet(s) Filed in Color)

(56) References Cited

OTHER PUBLICATIONS

Ma et al., "Paclitaxel Nano-Delivery Systems: A Comprehensive Review", Nanomedicine & Nanotechnology, vol. 4, Issue 2, 2013, 16 pages (with English-language Translation).
Office Action issued in Chinese Patent Application No. 201580001313.1 dated Feb. 17, 2017 (with English-language Translation).
International Search Report issued in PCT/JP2015/080316 dated Jan. 26, 2016.

* cited by examiner

Fig. 1
(A)
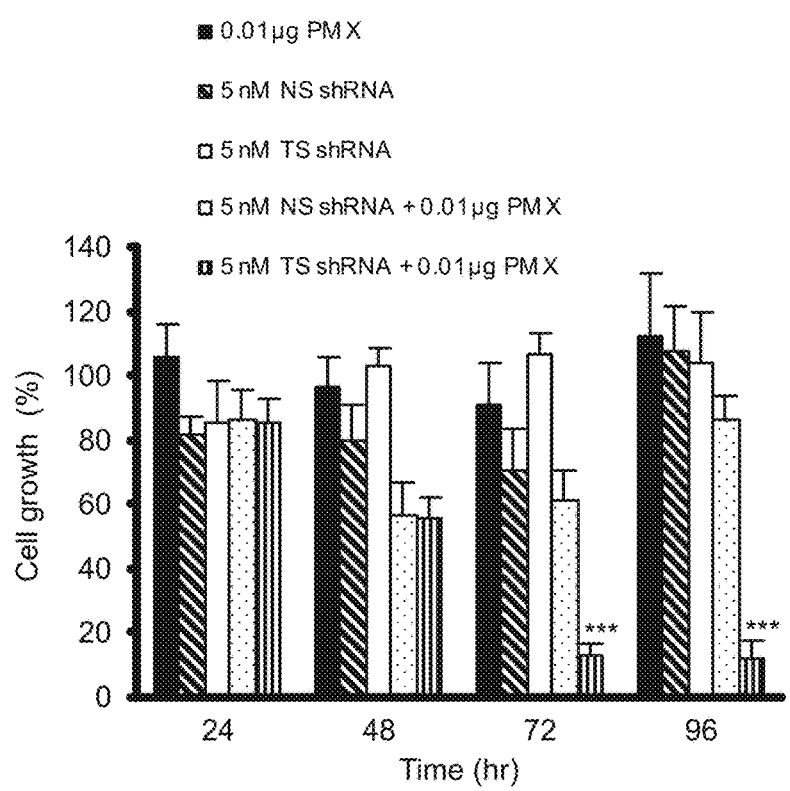
(B)
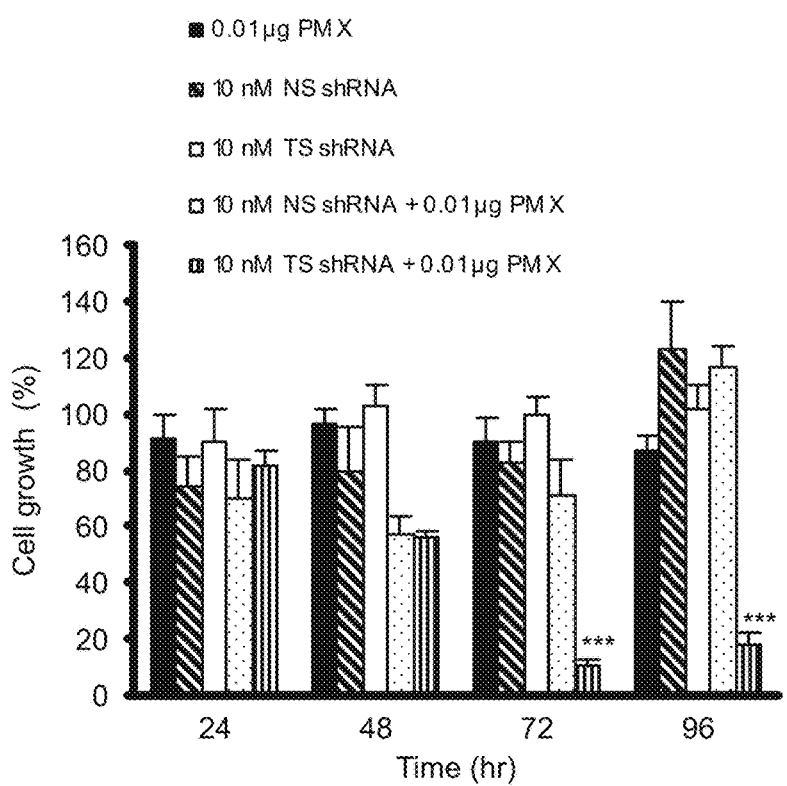

Fig. 2
(A)
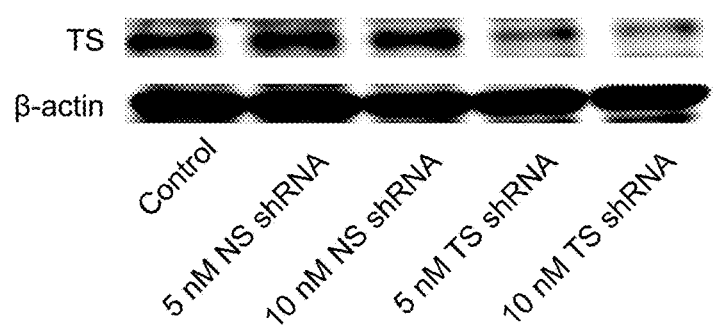
(B)
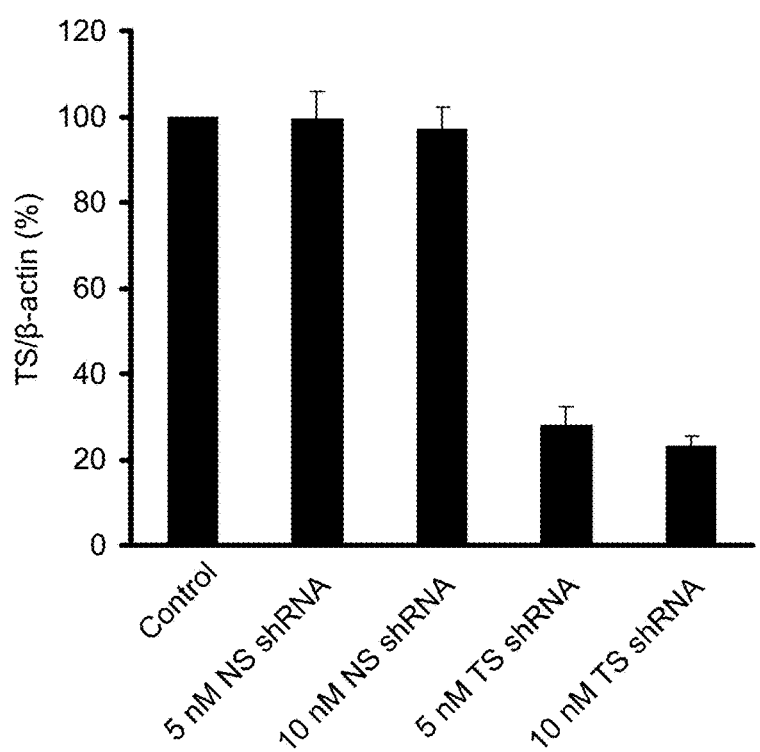

Fig. 6-1
(A) 20% DC-6-14
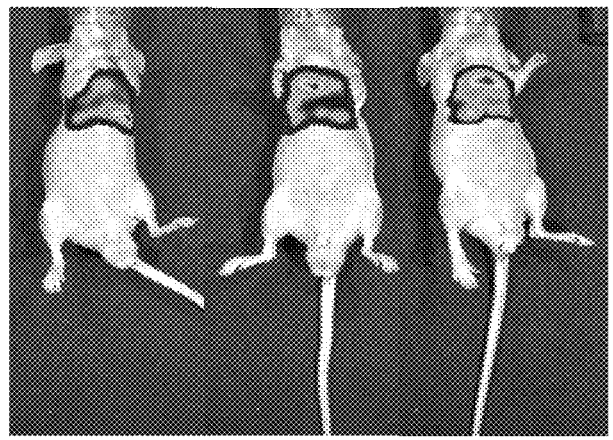
(B) 35% DC-6-14
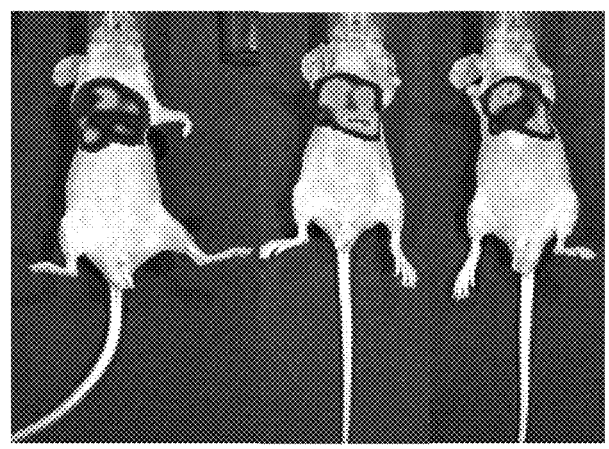
(C) 50% DC-6-14

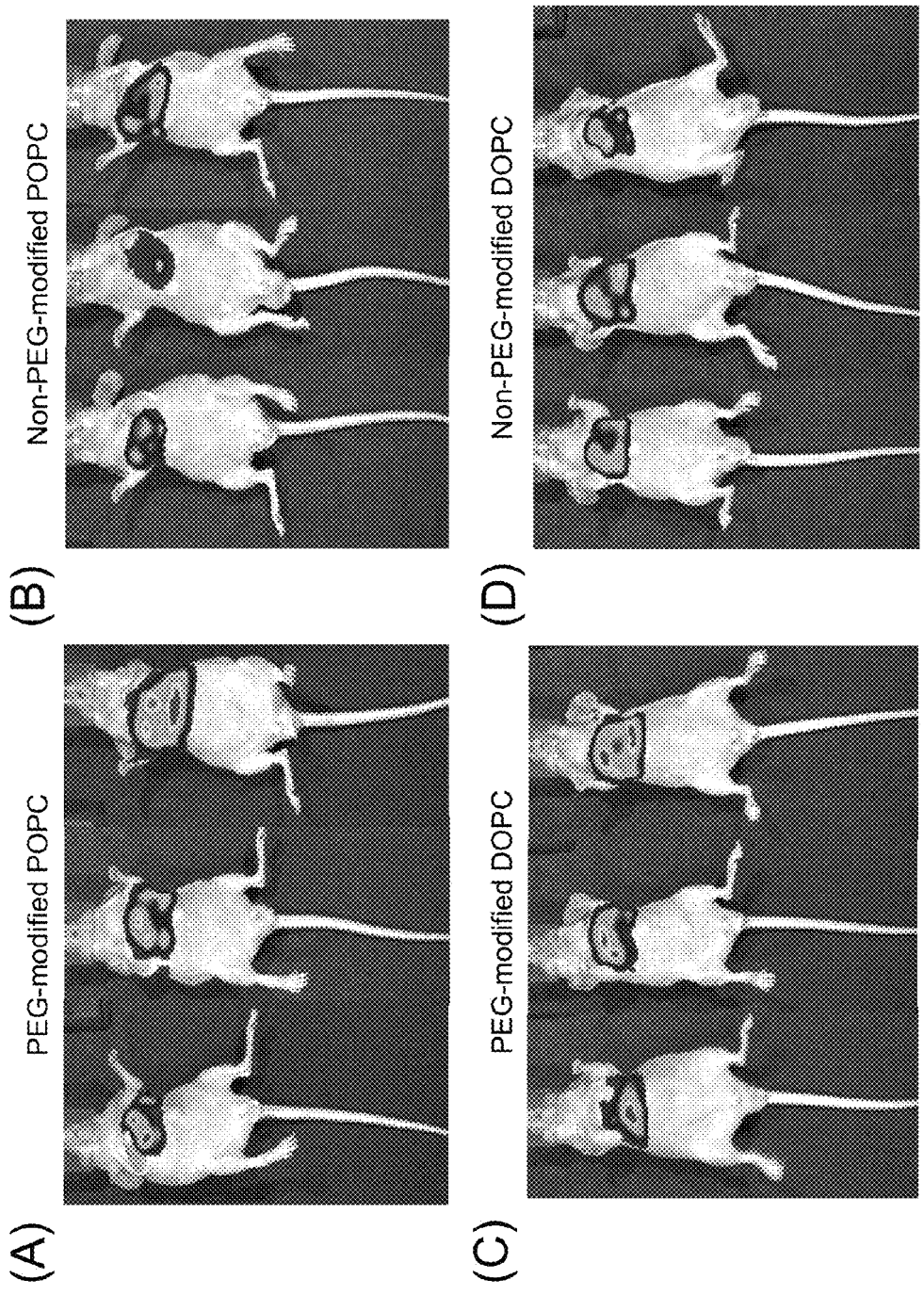

Fig. 8-4

| Treatment | MST (days) | ILS (%) |
|---|---|---|
| Control (9% sucrose) | 22.5 | - |
| NS shRNA lipoplex | 24.0 | 106.6% |
| TS shRNA lipoplex | 28.5 | 126.6% |
| PMX | 27.0 | 120.0% |
| PMX + NS shRNA lipoplex | 27.5 | 122.2% |
| PMX + TS shRNA lipoplex | 40 | 177.8% |

LIPOSOME FOR TOPICAL ADMINISTRATION AND APPLICATION THEREOF

REFERENCE TO SEQUENCE LISTING SUBMITTED VIA EFS-WEB

This application is includes an electronically submitted sequence listing in .txt format. The .txt file contains a sequence listing entitled "2016-03-07_1254-0578PUS1_ST25.txt" created on Mar. 7, 2016 and is 2,801 bytes in size. The sequence listing contained in this .txt file is part of the specification and is hereby incorporated by reference herein in its entirety.

TECHNICAL FIELD

The present invention relates to a liposome for topical administration and an antitumor agent using such liposome.

BACKGROUND ART

Liposomes are composed of phospholipids that constitute cell membranes of organisms, they have high biocompatibility, and they can deliver drugs and active ingredients while protecting them from degrading enzymes in vivo. Accordingly, liposomes have drawn attention as useful tools for drug delivery systems. In recent years, liposomes modified with polyethylene glycol (PEG) that improves retentivity in the blood and liposomes comprising, as constitutional lipids, hydrogenated phosphatidylcholine free of unsaturated bonds that enhances stability in the blood and strength and cholesterols that elevate the phase transition temperature of the membrane have been developed and generally used.

Meanwhile, RNAi molecules that induce RNA interference (hereafter referred to as "RNAi") have drawn attention as useful tools for tumor treatment and other purposes, and a wide variety of RNAi molecules that are capable of tumor growth inhibition have been developed. In addition, a method of using complexes composed of RNAi molecules and liposomes (i.e., lipoplexes) to deliver RNAi molecules as active ingredients to tumor cells has been developed (Qixin Leng et al., Drug Future, September 2009; 34 (9): 721; Sherry Y., Wu et al., The AAPS Journal, Vol. 11, No. 4, December 2009; and B. Ozpolat et al., Journal of Internal Medicine 267; 44-53, 2009).

In the past, the present inventors developed RNAi molecules targeting thymidylate synthases (hereafter referred to as "TS"), which is involved with DNA synthesis (WO 2010/113844). They reported that delivery of such RNAi molecules to the tumors via intravenous administration with the use of PEG-modified liposomes containing cholesterols at a given concentration would make it possible to inhibit the growth of tumors showing TS expression. They also reported that the use of such liposomes in combination with chemotherapeutic agents would result in tumor tropism improvement as well as the improvement of antitumor effects of RNAi molecules to a significant extent (WO 2012/161196).

However, development of a means that makes it possible to more efficiently introduce RNAi molecules capable of tumor growth inhibition into tumor cells has been awaited in the art.

SUMMARY OF THE INVENTION

It is an object of the present invention to provide a novel delivery system that can efficiently deliver an active ingredient to a target cell.

More specifically, it is an object of the present invention to provide a novel liposome that enables efficient delivery of an RNAi molecule capable of tumor growth inhibition to a tumor cell.

The present inventors have conducted concentrated studies in order to attain the above objects. As a result, they discovered that topical administration of a liposome that is composed of dioleylphosphatidylethanolamine (DOPE), phosphatidylcholine, and cationic lipid, that is not modified with PEG, that is free of cholesterols, and that comprises an active ingredient supported thereon to a region including a target cell or an area in the vicinity thereof would enable efficient delivery of an active ingredient to the target cell. This has led to the completion of the present invention.

Specifically, the present invention is as described below.

[1] A liposome for topical administration consisting of dioleylphosphatidylethanolamine (DOPE), phosphatidylcholine, and cationic lipid,
wherein the phosphatidylcholine has one or more features selected from (i) to (iii) below:
 (i) the phosphatidylcholine comprises at least one unsaturated fatty acid chain containing a carbon-to-carbon double bond;
 (ii) the phosphatidylcholine comprises at least one unsaturated fatty acid chain containing a cis-form carbon-to-carbon double bond; and
 (iii) the phosphatidylcholine has a phase transition temperature below 0° C.

[2] The liposome according to [1], wherein the cationic lipid is O,O'-ditetradecanoyl-N-(α-trimethylammonioacetyl)diethanolamine chloride (DC-6-14).

[3] The liposome according to [1], wherein the phosphatidylcholine is 1,2-dioleoyl-sn-glycero-3-phosphocholine (DOPC), palmitoyl-oeoyl phosphatidylcholine (POPC), or 1,2-dieicosenoyl-sn-glycero-3-phosphocholine (DEPC).

[4] The liposome according to [1], wherein the phosphatidylcholine is DOPC.

[5] The liposome according to [1], which consists of DOPE, DOPC, and DC-6-14.

[6] The liposome according to [5], which comprises DOPE, DOPC, and DC-6-14 at 3:2:5 by mole.

[7] A composition comprising the liposome according to any of [1] to [6] and an active compound.

[8] The composition according to [7], wherein the active compound is a nucleic acid.

[9] The composition according to [8], wherein the nucleic acid is bound to the outer membrane surface of the liposome.

[10] An antitumor agent comprising the liposome according to any of [1] to [6] and short hairpin RNA (shRNA) capable of inhibiting thymidylate synthase expression via RNAi.

[11] The antitumor agent according to [10], wherein the shRNA is bound to the outer membrane surface of the liposome.

[12] The antitumor agent according to [10], wherein the shRNA consists of the nucleotide sequence as shown in SEQ ID NO: 8.

[13] The antitumor agent according to [10], which is used in combination with cancer chemotherapy or a cancer chemotherapeutic agent.

[14] A combined product comprising the antitumor agent according to any of [10] to [13] and a cancer chemotherapeutic agent.

[15] The combined product according to [14], wherein the cancer chemotherapeutic agent is an antitumor agent having TS inhibitory action.

[16] The combined product according to [15], wherein the antitumor agent having TS inhibitory action is a 5-FU antitumor agent or pemetrexed sodium hydrate.

The present invention can provide a novel liposome that enables efficient delivery of an active ingredient to a target cell via topical administration thereof.

More specifically, the present invention can provide a novel liposome that enables efficient delivery of an RNAi molecule capable of tumor growth inhibition to a tumor cell via topical administration thereof.

This description includes part or all of the content as disclosed in the description and/or drawings of Japanese Patent Application No. 2013-095950, which is a priority document of the present application.

BRIEF DESCRIPTION OF THE DRAWINGS

The patent or application file contains at least one color drawing. Copies of this patent or patent application publication with color drawing will be provided by the USPTO upon request and payment of the necessary fee.

FIG. 1 shows the tumor growth inhibitory effects of a cancer chemotherapeutic agent, TS-shRNA, NS-shRNA, and shRNA in combination with a cancer chemotherapeutic agent on human malignant pleural mesothelioma cells. FIG. 1 (A) shows the results for shRNA at a final concentration of 5 nM, and FIG. 1 (B) shows the results for shRNA at a final concentration of 10 nM (***: $p<0.005$).

FIG. 2 shows the TS expression inhibitory effects of TS-shRNA and NS-shRNA in human malignant pleural mesothelioma cells. FIG. 2 (A) shows the results of Western blotting, and FIG. 2 (B) shows the results of quantification of the TS expression level on the basis of the results of Western blotting. The TS/β-actin ratio is represented in percentage form relative to 100%, which is assigned to the control sample without shRNA treatment.

FIG. 5-1 shows photographs demonstrating the results of a comparison of effects of Luc-shRNA introduction with the use of various cationic liposomes on tumor cells in orthotopic implantation mouse models of malignant pleural mesothelioma. In FIG. 5-1, (A) shows the results for the control (9% sucrose); (B) shows the results for a liposome containing DEPC (DEPC); (C) shows the results for a liposome containing DMPC (DMPC); (D) shows the results for a liposome containing DOPC (DOPC); and (E) shows the results for a liposome containing POPC (POPC).

FIG. 5-2 shows the results of quantification of effects of Luc-shRNA introduction with the use of various cationic liposomes on tumor cells in orthotopic implantation mouse models of malignant pleural mesothelioma on the basis of the results shown in FIG. 5-1 (*: $p<0.005$).

FIG. 6-1 shows photographs demonstrating the results of a comparison of effects of Luc-shRNA introduction with the use of various cationic liposomes with different DC-6-14 contents on tumor cells in orthotopic implantation mouse models of malignant pleural mesothelioma. In FIG. 6-1, (A) shows the results for a liposome with DC-6-14 content of 20%, (B) shows the results for a liposome with DC-6-14 content of 35%, and (C) shows the results for a liposome with DC-6-14 content of 50%, by mole.

FIG. 6-2 shows the results of quantification of effects of Luc-shRNA introduction with the use of various cationic liposomes with different DC-6-14 contents on tumor cells in orthotopic implantation mouse models of malignant pleural mesothelioma on the basis of the results shown in FIG. 6-1 (*: $p<0.005$).

FIG. 7-1 shows photographs demonstrating the results of a comparison of effects of Luc-shRNA introduction with the use of various PEG-modified and non-PEG-modified cationic liposomes on tumor cells in orthotopic implantation mouse models of malignant pleural mesothelioma. In FIG. 7-1, (A) shows PEG-modified POPC; i.e., the results for a liposome containing PEG-modified POPC, (B) shows non-PEG-modified POPC; i.e., the results for a liposome containing non-PEG-modified POPC, (C) shows PEG-modified DOPC; i.e., the results for a liposome containing PEG-modified DOPC, and (D) shows non-PEG-modified DOPC; i.e., the results for a liposome containing non-PEG-modified DOPC.

FIG. 7-2 shows the results of quantification of effects of Luc-shRNA introduction with the use of various cationic liposomes on tumor cells in orthotopic implantation mouse models of malignant pleural mesothelioma on the basis of the results shown in FIG. 7-1 (**: $p<0.01$).

FIG. 8-1 shows photographs demonstrating the results of a comparison of tumor growth inhibitory effects of a lipoplex having TS-shRNA bound to its outer membrane surface, a lipoplex comprising NS-shRNA bound to its outer membrane surface, a cancer chemotherapeutic agent (PMX), and a lipoplex in combination with a cancer chemotherapeutic agent (PMX) on tumor cells in orthotopic implantation mouse models of malignant pleural mesothelioma. In FIG. 8-1, (A) shows the results for the control (9% sucrose); (B) shows NS-shRNA; i.e., the results of treatment with a lipoplex comprising NS-shRNA bound to its outer membrane surface alone; (C) shows TS-shRNA; i.e., the results of treatment with a lipoplex having TS-shRNA bound to its outer membrane surface alone; (D) shows PMX; i.e., the results of treatment with a cancer chemotherapeutic agent alone; (E) shows PMX+NS-shRNA; i.e., the results of treatment with a cancer chemotherapeutic agent in combination with a lipoplex comprising NS-shRNA bound to its outer membrane surface; and (F) shows PMX+TS-shRNA; i.e., the results of treatment with a cancer chemotherapeutic agent in combination with a lipoplex having TS-shRNA bound to its outer membrane surface.

FIG. 8-2 shows the results of quantification of tumor growth inhibitory effects achieved by various treatments on tumor cells in orthotopic implantation mouse models of malignant pleural mesothelioma on the basis of the results shown in FIG. 8-1 (*: $p<0.05$; ***: $p<0.01$).

FIG. 8-3 shows the survival rates (%) of orthotopic implantation mouse models of malignant pleural mesothelioma subjected to treatment with the control (9% sucrose), a cancer chemotherapeutic agent (PMX) alone, a lipoplex comprising NS-shRNA bound to its outer membrane surface alone, a lipoplex having TS-shRNA bound to its outer membrane surface alone, or a lipoplex in combination with a cancer chemotherapeutic agent (PMX).

FIG. 8-4 shows the mean survival time (MST) and the increased life span (ILS) of orthotopic implantation mouse models of malignant pleural mesothelioma subjected to treatment with the control (9% sucrose), a lipoplex having TS-shRNA bound to its outer membrane surface alone, a lipoplex comprising NS-shRNA bound to its outer membrane surface alone, a cancer chemotherapeutic agent (PMX) alone, or a lipoplex in combination with a cancer chemotherapeutic agent (PMX).

In FIG. 11, (A) shows the results for the control (9% sucrose); (B) shows PMX; i.e., the results of treatment with a cancer chemotherapeutic agent alone; (C) shows TS preplex; i.e., the results of treatment with a preplex having TS-shRNA bound to its outer membrane surface alone; (D) shows PMX+TS preplex; i.e., the results of treatment with a cancer chemotherapeutic agent in combination with a preplex comprising NS-shRNA bound to its outer membrane surface; (E) shows TS lipoplex; i.e., the results of treatment with a lipoplex having TS-shRNA bound to its outer membrane surface alone; and (F) shows PMX+TS lipoplex; i.e., the results of treatment with a cancer chemotherapeutic agent in combination with a lipoplex comprising NS-shRNA bound to its outer membrane surface.

EMBODIMENTS FOR CARRYING OUT THE INVENTION

1. Liposome

Figure 3:
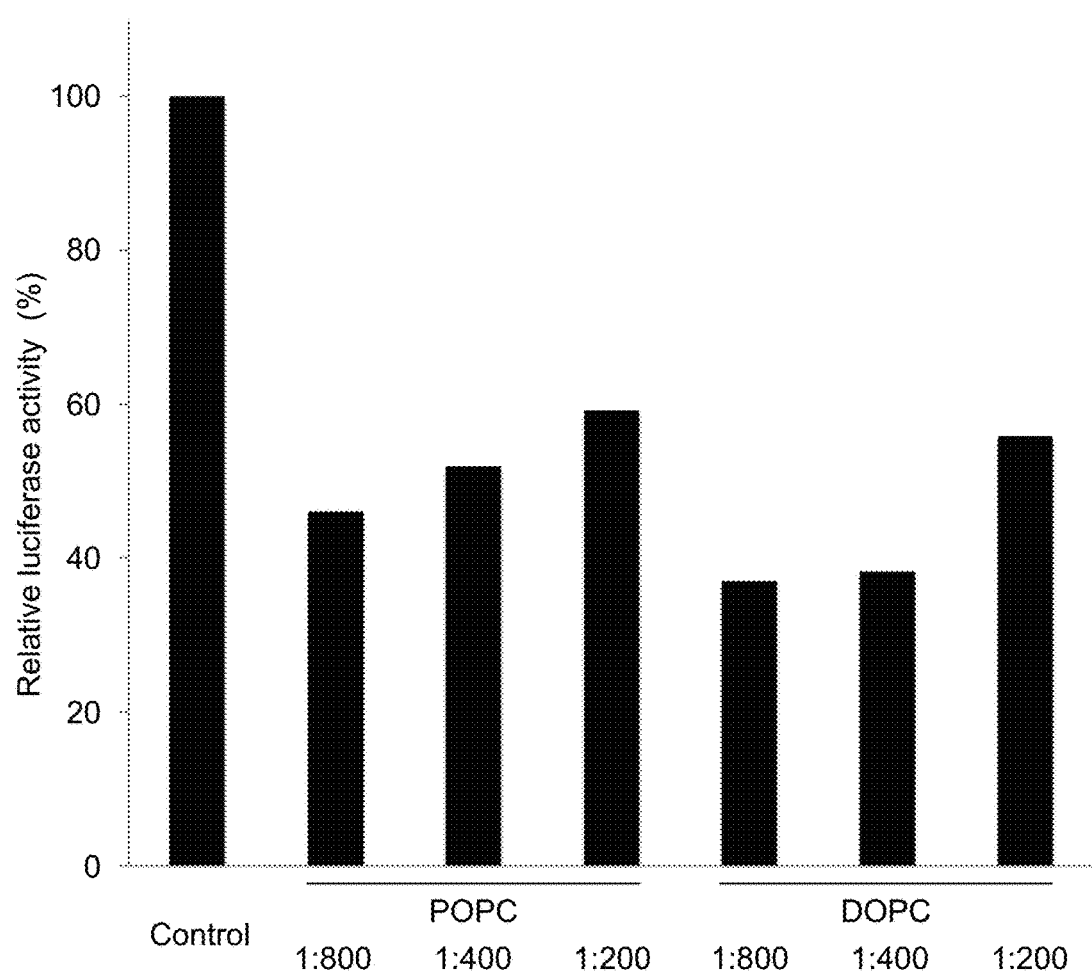
FIG. 3 shows the results of a comparison of effects of Luc-shRNA introduction with the use of various cationic liposomes via dual-luciferase assays.

The liposome of the present invention is in the form of a spherical hollow body consisting of a lipid bilayer consisting of dioleylphosphatidylethanolamine (DOPE), phosphatidylcholine, and cationic lipid.

The "phosphatidylcholine" that can be used in the present invention has one or more features selected from (i) to (iii) below:

(i) the phosphatidylcholine comprises at least one unsaturated fatty acid chain containing a carbon-to-carbon double bond;

(ii) the phosphatidylcholine comprises at least one unsaturated fatty acid chain containing a cis-form carbon-to-carbon double bond; and (iii) the phosphatidylcholine has a low phase transition temperature (e.g., below 0° C., below −10° C., or below −20° C.).

Examples of such "phosphatidylcholine" include 1,2-dioleoyl-sn-glycero-3-phosphocholine (DOPC), palmitoyl-oeoyl phosphatidylcholine (POPC), and 1,2-dieicosenoyl-sn-glycero-3-phosphocholine (DEPC), with DOPC being preferable.

The "cationic lipid" that can be used in the present invention can be any substance selected from among O,O'-ditetradecanoyl-N-(α-trimethylammonioacetyl)diethanolamine chloride (DC-6-14), N,N-dioleoyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleoyloxy)propyl)-N,N,N-trimethylammonium chloride (DOTMA), N,N-dimethyl-(2,3-dioleoyloxy)propylamine (DODMA), and a derivative of any thereof. Cationic lipid is preferably DC-6-14.

The liposome of the present invention preferably consists of DOPE, DOPC, and DC-6-14.

The proportion of DOPE, phosphatidylcholine (DOPC), and cationic lipid (DC-6-14) in the liposome can be preferably determined in a range of 2 to 4:1 to 3:4 to 6 by mole. The proportion of DOPE:DOPC:DC-6-14 is preferably 3:2:5.

The liposome of the present invention can be prepared in accordance with a conventional technique, such as thin-film shaking (the Bangham method) (A. D. Bangham et al., J. Mol. Biol., 13, 238-252, 1965; A. D. Bangham and R. W. Home, J. Mol. Biol., 8, 660-668, 1964). Specifically, phosphatidylethanolamine, phosphatidylcholine, and cationic lipid are separately dissolved in an organic solvent, such as chloroform, and they are collected and mixed in a container such as a flask to achieve the given composition described above. Subsequently, the organic solvent is evaporated to form a lipid layer at the bottom of the container, an aqueous solution such as a buffer is introduced thereinto, and the mixture is agitated to obtain a suspension containing the liposome. The "liposome" is occasionally referred to as a "cationic liposome" herein, and these terms are interchangeably used.

Alternatively, the liposome of the present invention is prepared by separately dissolving phosphatidylethanolamine, phosphatidylcholine, and cationic lipid in an organic solvent, such as chloroform, collecting them to achieve the give composition described above, adding an organic solvent (e.g., cyclohexane in an amount 5 to 30 times, preferably 5 to 15 times, and more preferably 10 times the amount of the total lipid by weight and an alcohol (preferably ethanol) in an amount 1% to 10%, preferably 1% to 5%, and more preferably 2% of the amount of cyclohexane by weight), and heating the mixture to 50° C. to 80° C., and preferably 65° C. to 75° C. to prepare a solution. Subsequently, the resulting solution is filtered, the organic solvent is frozen with the use of dry ice and acetone, the organic solvent is removed by drying treatment (it is grounded, according to need), and an aqueous solution such as a buffer is introduced thereinto. Thus, a suspension containing the liposome can be obtained. The thus-obtained liposome is occasionally referred to as a "presome" or "cationic presome" herein. A presome can be preserved in lyophilized form.

A particle size of the liposome of the present invention is 80 nm to 200 nm, and preferably about 100 nm. The zeta potential of the liposome of the present invention is 40 to 60 mV, and preferably about 50 mV. When the liposome of the present invention is the presome, a particle size thereof is 100 nm to 600 nm, and preferably about 100 nm to 200 nm.

The liposome of the present invention can be used as a carrier for topical administration of an active ingredient. In the present invention, "topical administration" is aimed at administration of an active ingredient directly to an affected area, a lesion, and/or an area in the vicinity thereof, so as to allow the active ingredient to act on the affected area or lesion. In the present invention, accordingly, "topical administration" is not intended to systemic administration of an active ingredient via intravenous injection or other means. Examples of topical administration include, but are not limited to, intramuscular, intraperitoneal, intrathoracic, hypodermic, endodermic, intraocular, intracerebral, intrathecal, intravaginal, intrarectal, intraorgan, and intratumoral injections and application to the epidermis. The term "topical administration" preferably refers to intracavitary administration, and more preferably intrathoracic or intraperitoneal administration. The term "active ingredient" refers to an active ingredient of a pharmaceutical or cosmetic product. Examples thereof include DNA, RNA, a DNA-RNA hybrid, a protein, a peptide, and a compound.

2. Composition

The composition of the present invention comprises the liposome of the present invention and the active ingredient, and such composition can be used for topical administration of the active ingredient.

Examples of active ingredients include those exemplified above. For example, active ingredients can be siRNA or shRNA that is capable of inhibiting expression of genes encoding factors expressed in tumor cells and involved with tumor cell growth via RNAi, although active ingredients are not particularly limited thereto. Examples of "genes encoding factors expressed in tumor cells and involved with tumor cell growth" include, but are not limited to, genes encoding growth regulatory factors, such as thymidylate synthase, VEGF, EGFR, PDGF, HGF, Wnt, Bcl-2, and survivin, and enzymes involved in nucleic acid synthesis, such as ribonucleotide reductase and DNA polymerase. Gene information on these genes is disclosed in known databases of GenBank and the like, and siRNA or shRNA can be designed and synthesized on the basis of such gene information. shRNA that is described in detail below can be used as shRNA that can inhibit expression of thymidylate synthase via RNAi. Alternatively, an anticancer agent or cancer chemotherapeutic agent can be used as an active ingredient.

In the composition of the present invention, an active ingredient may be contained in a hollow portion enclosed by a lipid bilayer of a liposome, or it may be bound to the outer membrane surface of a lipid bilayer. An active ingredient is preferably bound to the outer membrane surface of a lipid bilayer of a liposome.

The composition of the present invention may also contain, in addition to the liposome and the active ingredient, an excipient, a binder, a disintegrant, a lubricant, a diluent, a solubilizer, a suspending agent, an isotonizing agent, a pH regulator, a buffer, a stabilizer, a colorant, a flavoring agent, an odor improving agent, histidine, or other substances that are generally used in the production of pharmaceutical or cosmetic products.

Examples of excipients include lactose, sucrose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerine, sodium alginate, gum Arabic, and a mixture thereof. Examples of lubricants include purified talc, stearate, sodium borate, polyethylene glycol, and a mixture thereof. Examples of binders include simple syrup, glucose solution, starch solution, gelatin solution, polyvinyl alcohol, polyvinyl ether, polyvinyl pyrrolidone, carboxymethylcellulose, shellac, methylcellulose, ethylcellulose, water, ethanol, potassium phosphate, and a mixture thereof. Examples of disintegrants include dry starch, sodium alginate, agar powder, laminaran powder, sodium bicarbonate, calcium carbonate, polyoxyethylene sorbitan fatty acid esters, sodium lauryl sulfate, stearic acid monoglyceride, starch, lactose, and a mixture thereof. Examples of diluents include water, ethyl alcohol, macrogol, propylene glycol, ethoxylated isostearyl alcohol, polyoxylated isostearyl alcohol, polyoxyethylene sorbitan fatty acid esters, and a mixture thereof. Examples of stabilizers include sodium pyrosulfife, ethylenediaminetetraacetic acid, thioglycolic acid, thiolactic acid, and a mixture thereof. Examples of isotonizing agents include sodium chloride, boric acid, glucose, glycerine, and a mixture thereof. Examples of pH regulators and buffers include sodium citrate, citric acid, sodium acetate, sodium phosphate, and a mixture thereof.

The composition of the present invention can be prepared in a dosage form suitable for topical administration, and it can be prepared in any of various forms, such as an injection, a suspension, an emulsion, an ointment, a cream, or a tablet.

3. Antitumor Agent

The antitumor agent of the present invention comprises the liposome of the present invention and, as an active ingredient, shRNA that can inhibit expression of thymidylate synthase (hereafter referred to as "TS") via RNAi.

shRNA that can inhibit TS expression according to the present invention exerts TS-specific RNAi activity by targeting mRNA of TS, and it can thus inhibit TS expression remarkably. The term "targeting mRNA" used herein refers to the situation in which an antisense strand of shRNA described in detail below can hybridize under stringent conditions to the target mRNA.

Stringent conditions can be determined on the basis of the melting temperature (Tm) for nucleic acid at which a hybrid is formed in accordance with a conventional technique. Under stringent conditions, for example, washing conditions that allows maintenance of hybridization comprise generally "1×SSC, 0.1% SDS, 37° C.," more strictly "0.5×SSC, 0.1% SDS, 42° C.," and further strictly "0.1×SSC, 0.1% SDS, 65° C."

According to the present invention, shRNA comprises a sense strand comprising a nucleotide sequence identical to the nucleotide sequence of ORF encoding TS or a part thereof and an antisense strand hybridizing under stringent conditions to the sense strand. The term "nucleotide sequence identical to the nucleotide sequence of ORF or a part thereof" refers to a nucleotide sequence that is identical to a nucleotide sequence obtained by substituting thymine with uracil in the nucleotide sequence of ORF or a part thereof.

The sense strand consists of 15 to 25 nucleotides, and preferably 19 nucleotides. While the nucleotide sequence of the sense strand is preferably the same as the nucleotide sequence of ORF encoding TS, it may be substantially the same sequence; that is, a homologous sequence. Specifically, the nucleotide sequence of the sense strand may be different from the nucleotide sequence of ORF by substitution, deletion, insertion, and/or addition of one or more; that is, 1 to 3 nucleotides, preferably 1 or 2 nucleotides, and more preferably 1 nucleotide.

The antisense strand comprises a nucleotide sequence that can hybridize under stringent conditions to the sense strand. As long as it can hybridize under stringent conditions, the antisense strand may comprise a mismatch, including substitution, deletion, insertion, and/or addition of 1 to 3 nucleotides, preferably 1 or 2 nucleotides, and more preferably 1 nucleotide. The antisense strand preferably consists of a nucleotide sequence completely complementary to the sense strand.

Nucleotide sequences of the sense strand and the antisense strand can be selected on the basis of the known TS-encoding nucleotide sequence (GenBank: CR601528.1). Various methods for selecting such nucleotide sequences are known. For example, the siRNA Design Support System (Takara Bio Inc.) can be employed.

In the present invention, examples of sense strands include those consisting of the nucleotide sequences indicated below, although sense strands are not limited thereto:

```
                                         (SEQ ID NO: 1)
5'-GUAACACCAUCGAUCAUGA-3';

(SEQ ID NO: 3)
5'-GAAUACAGAGAUAUGGAAU-3';

(SEQ ID NO: 5)
5'-CGAUCAUGAUGUAGAGUGU-3';
and (SEQ ID NO: 9)
5'-GGGUGUUUUGGAGGAGUUGTT-3'.
```

In the present invention, shRNA preferably comprises: the sense strand 5'-GUAACACCAUCGAUCAUGA-3' (SEQ ID NO: 1) and the antisense strand 5'-UCAUGAUCGAUG-GUGUUAC-3' (SEQ ID NO: 2); the sense strand 5'-GAAUACAGAGAUAUGGAAU-3' (SEQ ID NO: 3) and the antisense strand 5'-AUUCCAUAUCUCUGUAUUC-3' (SEQ ID NO: 4); the sense strand 5'-CGAUCAUGAUGUA-GAGUGU-3' (SEQ ID NO: 5) and the antisense strand 5'-ACACUCUACAUCAUGAUCG-3' (SEQ ID NO: 6); or the sense strand 5'-GGGUGUUUUGGAGGAGUUGTT-3' (SEQ ID NO: 9) and the antisense strand 5'-AACAACUC-CUCCAAAACACCC-3' (SEQ ID NO: 10).

In the present invention, shRNA more preferably comprises the sense strand consisting of the nucleotide sequence as shown in SEQ ID NO: 1 and the antisense strand consisting of the nucleotide sequence as shown in SEQ ID NO: 2.

A sense strand and an antisense strand are connected to each other through a linker, they are folded when the linker forms a loop, and the antisense strand and the sense strand hybridize to each other to form a double-stranded portion. As long as a linker included in the shRNA molecule can connect the sense strand to the antisense strand and form a stem-loop structure, it may be a polynucleotide or non-polynucleotide linker. A linker is preferably, but is not particularly limited to, a polynucleotide linker consisting of 2 to 22 nucleotides known in the art. Specific examples thereof include UAGUGCUCCUGGUUG (SEQ ID NO: 7), UUCAAGAGA, CCACC, CUCGAG, CCACACC, UUCAAGAGA, AUG, CCC, and UUCG, with UAGUG-CUCCUGGUUG (SEQ ID NO: 7) being preferable.

In the present invention, shRNA comprises an overhang consisting of two or more nucleotides at the 3' end.

In the present invention, the term "overhang" refers to a nucleotide added to the 3' end of the antisense strand that does not have a nucleotide capable of complementarily binding to a corresponding position of the sense strand. If an antisense strand does not have an overhang at the 3' end, the degree of TS expression inhibition caused by shRNA decreases by about 40% to 60% upon transfection with the use of the liposome of the present invention, compared with a case in which an antisense strand has an overhang at the 3' end. Types and numbers of nucleotides constituting the overhang are not particularly limited. For example, sequences consisting of 1 to 5, preferably 1 to 3, and more preferably 1 or 2 nucleotides can be used. Specific examples include TTT, UU, and TT, with UU being preferable.

In the present invention, preferable shRNA is single-stranded RNA consisting of the nucleotide sequence as shown in SEQ ID NO: 8.

The sense or antisense strand may have the phosphorylated 5' end, and it may comprise triphosphate (ppp) bound to the 5' end, according to need.

shRNAs are covalently or non-covalently bound to the outer membrane surface of the lipid bilayer of the liposome of the present invention. In order to bind shRNAs to the liposome, it is preferable that a mixture containing the shRNAs and the liposome be vigorously agitated for 1 to 15 minutes, and preferably about 10 minutes (e.g., via ultrasonic agitation). Thus, a particle size of the resulting liposome comprising shRNA can be adjusted to several hundred nanometers (Barichello, J. M., et al., Int. J. Pharm., 2011). Through agitation, in addition, shRNAs can be uniformly dispersed and bound to the liposome. This can prevent tissues from irregular uptake of liposomes caused by non-uniform shRNA binding. When a liposome is a presome, alternatively, shRNA is added to a suspension containing the presome and mixed (e.g., via vortex), so as to bind shRNA to the outer membrane surface of the lipid bilayer of the presome.

In the present invention, a particle size of a liposome having shRNA is 200 nm to 600 nm, and preferably about 300 nm to 400 nm. In the present invention, also, a particle size of a presome having shRNA is 200 nm to 2 µm, and preferably about 300 nm to 1 µm. In the present invention, the zeta potential of a liposome having shRNA is 0 to 50 mV, and preferably about 25 to 35 mV.

The liposome having shRNA of the present invention may comprise siRNA or shRNA that can inhibit the expression of genes encoding factors expressed in tumor cells and involved with tumor cell growth via RNAi, in addition to shRNA that can inhibit TS expression. siRNA or shRNA as defined above can be used. shRNA that can inhibit TS expression and another siRNA or shRNA may be bound to the same liposome, or they may be bound to different liposomes.

In this description, a liposome having shRNA is occasionally referred to as a "lipoplex," and a presome having shRNA is occasionally referred to as a "preplex."

As described in detail in the examples below, the liposome having shRNA is capable of inhibiting tumor cell growth through topical administration thereof, and it can accordingly be used for treatment of cancer.

Cancers that can be treated with the use of the antitumor agent of the present invention are those exhibiting high TS expression levels. Examples thereof include, but are not particularly limited to, colorectal cancer, liver cancer, renal cancer, head and neck cancer, esophageal cancer, gastric cancer, biliary tract cancer, gallbladder and bile duct cancer, pancreatic cancer, lung cancer, breast cancer, ovarian cancer, uterine cervix cancer, uterine body cancer, bladder cancer, prostate cancer, malignant pleural mesothelioma, testicular tumor, ovarian cancer, osteosarcoma or soft-tissue osteosarcoma, skin cancer, and brain tumor. Carcinomatous pleurisy and carcinomatous peritonitis can be treated with the use of the antitumor agent of the present invention. Candidates for treatment are, for example, preferably gastric cancer, lung cancer, biliary tract cancer, liver cancer, malignant pleural mesothelioma, ovarian cancer, carcinomatous peritonitis, and carcinomatous peritonitis, and particularly preferably malignant pleural mesothelioma, non-small cell lung cancer without distant metastasis, carcinomatous pleurisy, gastric cancer peritoneal metastasis, ovarian cancer peritoneal metastasis, and carcinomatous peritonitis.

The antitumor agent of the present invention may further comprise, in addition to a liposome having shRNA, an excipient, a binder, a disintegrant, a lubricant, a diluent, a solubilizer, a suspending agent, an isotonizing agent, a pH regulator, a buffer, a stabilizer, a colorant, a flavoring agent, an odor improving agent, histidine, or other substances that are generally used in the production of pharmaceutical products. The excipient, the lubricant, the binder, the disintegrant, the diluent, the stabilizer, the isotonizing agent, and the pH regulator defined above can be used.

The antitumor agent of the present invention can be administered by means of topical administration. Forms of topical administration are as defined above. The composition of the present invention can be prepared in any of various dosage forms suitable for topical administration, such as an injection, a suspension, an emulsion, or a spray.

Effects of the antitumor agent of the present invention can be evaluated by administering the antitumor agent to cells or tissues originating from any of the cancers described above and to an individual afflicted with any of the cancers described above, comparing the size of the resulting tumor with the size of the tumor in cells or tissues and an individual to which the antitumor agent has not been administered (or prior to administration), and using the contraction or extinction of the tumor as the indicator. Alternatively, effects of the antitumor agent of the present invention can be evaluated by administering the antitumor agent to cells or tissues originating from any of the cancers described above and to an individual afflicted with any of the cancers described above, and determining the improved survival rate (i.e., life-prolonging effects) and reduction or disappearance of a pleural effusion or ascites, in comparison with an individual to which the antitumor agent has not been administered.

The antitumor agent of the present invention can be used in combination with existing cancer chemotherapy or a cancer chemotherapeutic agent. Cancer chemotherapy or a cancer chemotherapeutic agent that can be used in combination with the antitumor agent of the present invention is not particularly limited, provided that it can modify tumor conditions, so that the liposome of the present invention can easily invade into tumor tissue. An example of existing cancer chemotherapy is a chemotherapy involving the use of "an antitumor agent having TS inhibitory action" described below, and an example of an existing cancer chemotherapeutic agent is an antitumor agent having TS inhibitory action.

An "antitumor agent having TS inhibitory action" is not particularly limited, provided that it can inhibit TS functions. Examples thereof include a 5-FU antitumor agent, pemetrexed sodium hydrate, raltitrexed (Tomudex), and methotrexate (MTX).

The correlation between the TS expression level and a response to the 5-FU antitumor agent has been reported (Patrick G. Johnston et al., Cancer Res., 1995; 55: 1407-12; and Kun-Huei Yeh et al., Cancer 1998; 82: 1626-31). Among cancer patients, those exhibiting a relatively low TS expression level show a remarkable response to the 5-FU antitumor agent. In contrast, many cancer patients exhibiting relatively enhanced TS expression levels are tolerant to the 5-FU antitumor agent. A similar correlation is observed between pemetrexed sodium hydrate and the TS expression levels. Through administration of the antitumor agent of the present invention, TS production in tumor tissues can be suppressed, and a response of the tumor tissues to the antitumor agent having TS inhibitory action can be enhanced. When the antitumor agent of the present invention is used in combination with an antitumor agent having TS inhibitory action, the antitumor agent of the present invention is selectively accumulated in tumors, and shRNA can be efficiently delivered to the tumor cells. With the use of the antitumor agent of the present invention in combination with the antitumor agent having TS inhibitory action, accordingly, antitumor effects can be remarkably higher than those achieved with the use of the antitumor agent having TS inhibitory action or the antitumor agent of the present invention alone.

Examples of 5-FU antitumor agents include 5-FU and a 5-FU derivative from which 5-FU is produced as an active metabolite. An example of a 5-FU derivative is an agent containing tegafur. A 5-FU derivative is preferably a tegafur-containing compound, and specific examples thereof include a compound drug of tegafur and uracil (e.g., UFT®, Taiho Pharmaceutical Co., Ltd.) and a compound drug of tegafur, gimeracil, and oteracil potassium. Among these, a compound drug of tegafur, gimeracil, and oteracil potassium, such as TS-1® (Taiho Pharmaceutical Co., Ltd.), is particularly preferable.

An example of pemetrexed sodium hydrate is Alimta® (Eli Lilly Japan K.K.). As with the case of the 5-FU antitumor agent, antitumor effects achieved with the use of the pemetrexed sodium hydrate in combination with the antitumor agent of the present invention are remarkably higher than those achieved with the use of the pemetrexed sodium hydrate or the antitumor agent of the present invention alone.

The antitumor agent of the present invention can be used in combination with other conventional cancer chemotherapeutic agents, in addition to or instead of the antitumor agent having TS inhibitory action. Examples of such cancer chemotherapeutic agents include cyclophosphamide, nitrogen mustard N-oxide, ifosfamide, melphalan, busulphan, mitobronitol, carboquone, thiotepa, ranimustine, nimustine, temozolomide, carmustine, pemetrexed disodium, methotrexate, 6-mercaptopurine riboside, mercaptopurine, doxifluridine, carmofur, cytarabine, cytarabine ocfosfate, enocitabine, gemcitabine, fludarabine, pemetrexed, cisplatin, carboplatin, oxaliplatin, paclitaxel, docetaxel, irinotecan hydrochloride, and capecitabine. One or a plurality of cancer chemotherapeutic agents selected therefrom can be used. As in the case of the antitumor agent having TS inhibitory action, shRNA can be efficiently delivered to tumor cells when the cancer chemotherapeutic agent is used in combination with the antitumor agent of the present invention. Antitumor effects achieved thereby can be remarkably higher than those achieved with the use of the cancer chemotherapeutic agent or the antitumor agent of the present invention alone.

As long as the antitumor agent of the present invention is administered in combination with the existing cancer chemotherapeutic agent, these agents can be provided in the form of a "combined product."

The antitumor agent of the present invention can be prepared in the form of a "combined product" in combination with the existing cancer chemotherapeutic agent. Such "combined product" may be a compound drug containing the antitumor agent of the present invention and the existing cancer chemotherapeutic agent as active ingredients. In addition, a single package (a formulation kit) containing the antitumor agent of the present invention and the existing cancer chemotherapeutic agent suitable for combined administration can be produced, packaged, and distributed.

The term "combined administration" can refer to not only simultaneous administration of the antitumor agent of the present invention and the existing cancer chemotherapeutic agent but also administration of the antitumor agent of the present invention and the existing cancer chemotherapeutic agent at certain intervals. The route of administration and the means for administration of the antitumor agent of the present invention may be the same or different from those of the existing cancer chemotherapeutic agent.

The dose and the administration frequency of the antitumor agent of the present invention can vary depending on factors, such as the age and the body weight of a patient and the severity of disease. The antitumor agent can be administered at a single dose appropriately selected from the range of 0.0001 mg to 100 mg in terms of the amount of shRNA per kg of the body weight 1 to 3 times every day or every 1 to 21 days.

The dose of the existing cancer chemotherapeutic agent can vary depending on factors, such as a type of a chemical substance as an active ingredient, the age and the body weight of a patient, and the severity of disease. The existing cancer chemotherapeutic agent can be administered at a single dose appropriately selected from the range of 0.0001 mg to 1000 mg per kg of the body weight 1 to 3 times every day or every 1 to 14 days. When the existing cancer chemotherapeutic agent is a 5-FU antitumor agent, for example, it can be administered at a daily dose of 60 to 160 mg in terms of tegafur every day or every 1 to 7 days. When the existing cancer chemotherapeutic agent is pemetrexed sodium hydrate, it can be administered at a daily dose of 500 to 1000 mg every day or every 1 to 7 days. The existing cancer chemotherapeutic agent can be administered at lower doses and frequencies when used in combination with the antitumor agent of the present invention compared with a case in which it is administered alone. This can suppress or delay the development of side effects that can be caused by administration of the existing cancer chemotherapeutic agents. Examples of side effects include, but are not limited to, bone-marrow suppression, hemolytic anemia, disseminated intravascular coagulation syndrome, fulminant hepatic failure, dehydration, enteritis, interstitial pneumonia, stomatitis, gastrointestinal tract ulcer, gastrointestinal tract hemorrhage, perforation of the gastrointestinal tract, acute renal failure, muco-cutaneo-ocular syndrome, toxic epidermal necrolysis, psychoneurotic disorder, acute pancreatitis, rhabdomyolysis, and anosmia.

4. Method of Treatment

The present invention also relates to a method for treating cancer using the antitumor agent of the present invention. Examples of cancers that can be treated by the method include the cancers defined above. In the method of the present invention, the routes of administration and the dosages of the antitumor agent of the present invention and the existing cancer chemotherapeutic agents are as described above.

EXAMPLES

Hereafter, the present invention is described in greater detail with reference to the examples below, although the present invention is not limited to these examples.

Example 1

Inhibitory Effects on Cell Growth with the Use of TS-Targeting shRNA in Combination with Alimta In Vitro (TS-Targeting shRNA)

TS-targeting shRNA (hereafter referred to as "TS-shRNA") having the sequence demonstrated below was synthesized on the basis of the known shRNA capable of inhibiting TS expression that has been confirmed to have the antitumor effects (see WO 2012/161196).

```
TS-shRNA:
                                        (SEQ ID NO: 8)
5'-GUAACACCAUCGAUCAUGAUAGUGCUCCUGGUUGUCAUGAUCGAUG

GUGUUACUU-3'
```

In contrast, shRNA having the sequence demonstrated below that does not target any mRNA was used as a control. Hereafter, the control shRNA is referred to as "NS-shRNA."

```
NS-shRNA:
                                       (SEQ ID NO: 11)
5'-UCUUAAUCGCGUAUAAGGCUAGUGCUCCUGGUUGGCCUUAUACGCG

AUUAAGAUU-3'
```

(MTT Assay)

This experiment was carried out on a 96-well plate scale. Transfection was carried out using Lipofectamine® RNAi MAX (hereafter referred to as "Lf RNAi MAX"), which is a cationic liposome, in accordance with the manufacturer's instructions.

shRNA (300 pmol of TS-shRNA or NS-shRNA) and 15 µl of Lf RNAi MAX were separately diluted with OptiMEM to prepare solutions (500 nl each), the resulting solutions were mixed with each other, and the mixture was allowed to stand at room temperature for 10 to 20 minutes to form a complex (i.e., a lipoplex). A suspension of human malignant pleural mesothelioma cells (MSTO-211H) (2,000 cells/100 nl) was added to wells, 50 µl of lipoplex was added thereto 24 hours thereafter, and the final total volume was adjusted to 150 µl (the final shRNA concentration in the wells was adjusted to 5 nM or 10 nM). The medium was removed 24 hours after the initiation of transfection, and 200 µl of a fresh medium containing or not containing an existing cancer chemotherapeutic agent ("Alimta," pemetrexed sodium hydrate, PMX, Eli Lilly) at 0.01 µg/ml was added thereto. The medium was removed 0, 24, 48, 72, and 96 hours after the addition of the fresh medium. A 0.5% MTT (3-(4,5-dimethylthiazol-2-yl)-2,5-diphenyltetrazolium bromide) solution (50 µl) was added thereto, and incubation was then carried out at 37° C. in the presence of 5% $CO_2$ for 4 hours. Also, the 0.5% MTT solution was added to cell-free wells to obtain a background.

After the completion of incubation, acidic isopropanol (150 µl) was added to each well. Formazan crystals were dissolved using a shaker. Absorbance was determined at a wavelength of 570 nm using a plate reader. The cell growth rate was then calculated using the equation demonstrated below.

Cell growth rate (%)=[$A570$($X$ hours after the addition of fresh medium)/$A570$(0 hours after the addition of fresh medium)]×100

Figures 1, 5:
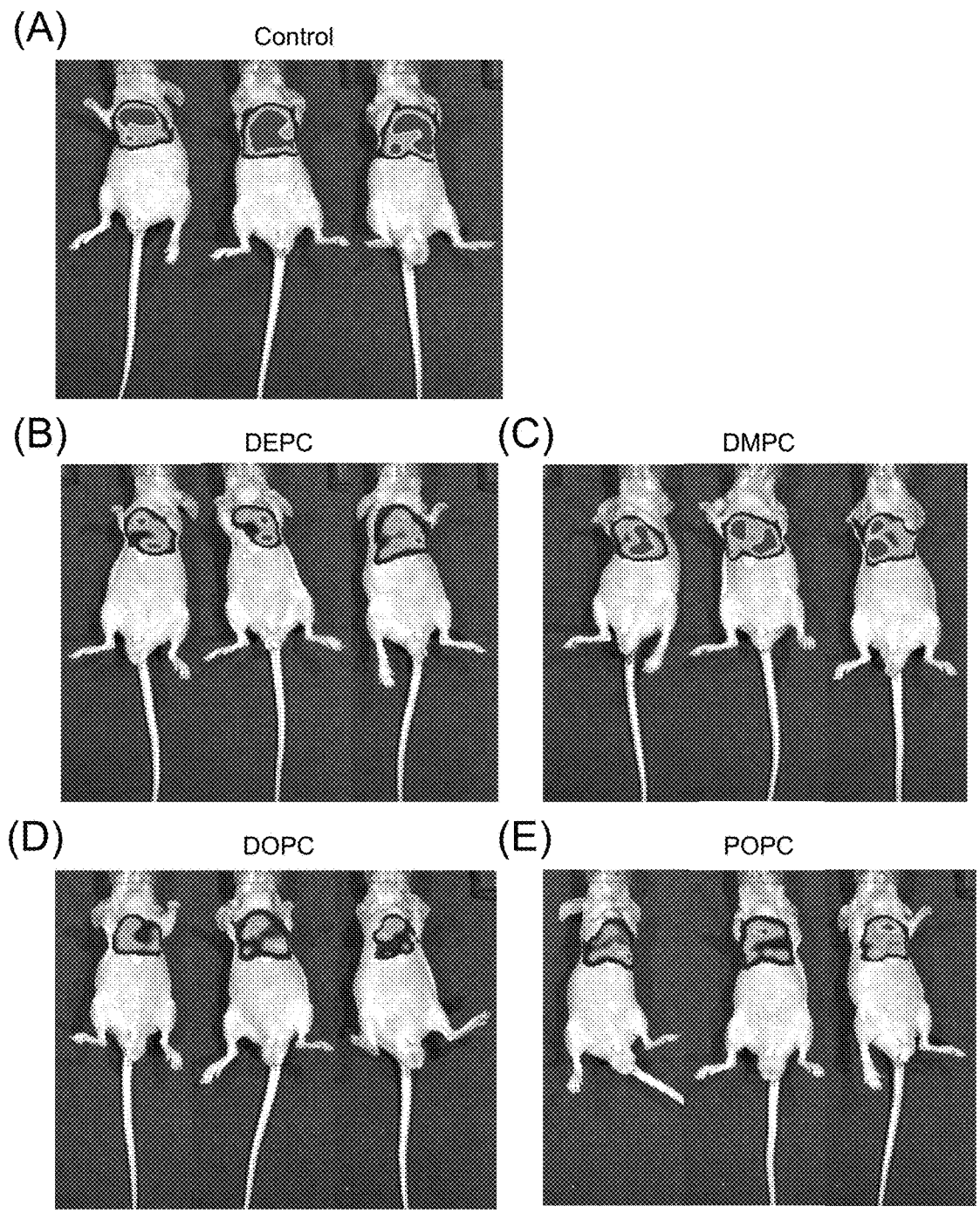

The results are shown in FIG. 1.

As shown in FIG. 1, TS-shRNA inhibited the growth of MSTO-211H cells to a significant extent in the presence of PMX in a time-dependent manner.

Example 2

Inhibition of TS Expression by TS-shRNA (Transfection)

Transfection was carried out using Lipofectamine® RNAi MAX (hereafter referred to as "Lf RNAi MAX"), which is a cationic liposome, in accordance with the manufacturer's instructions.

The lipoplex prepared in Example 1 was used herein.

A suspension of MSTO-211H cells (10 ml) was seeded on a 10-cm dish (500,000 cells/dish), and culture was conducted for 24 hours in advance. Each lipoplex was directly added thereto, so as to adjust the final total volume to 15 ml, followed by transfection. The final concentration of TS-shRNA or NS-siRNA was adjusted to 5 or 10 nM. The control was not treated with shRNA. After the initiation of transfection, culture was carried out in a medium at 37° C. in the presence of 5% $CO_2$ for 72 hours, and the cell extract was then prepared by the method described below.

(Preparation of Cell Extract)

Seventy two hours after the initiation of transfection, the medium was removed, followed by washing with cool PBS(−). Thereafter, cells were detached from the dish using a trypsin solution, and the supernatant was removed by centrifugation. Further, washing with cool PBS(−) was carried out, and 100 to 150 μl of cool lysis buffer (50 mM Tris-HCl (pH 7.4), 1% NP-40, 0.25% sodium deoxycholate, 150 mM NaCl, and Protease Inhibitor Cocktail (Sigma-Aldrich, MO, U.S.A.)) was added thereto. Incubation was then carried out on ice (4° C. for 1 hour) for cell lysis. Subsequently, centrifugation was performed (15,000×g, 15 minutes, 4° C.), and the obtained supernatant was used as a cell extract.

(Preparation of SDS-PAGE Sample)

The above cell extract was mixed with the equivalent amount of a 2× sample buffer, and the resultant was heated using a microtube hot plate at 95° C. for 3 minutes. Subsequently, centrifugation was performed for 30 seconds, followed by cooling to room temperature. Thus, an SDS-PAGE sample was obtained.

(SDS-PAGE)

The sample (6 μl corresponding to 9 μg of protein/lane) was applied to 12% polyacrylamide gel, the gel was connected to a power supply (Bio-Rad laboratories), and electrophoresis was performed for about 80 minutes at a constant current of 40 mA for two gel sheets (20 mA for a single gel sheet).

(Western Blotting)

Filter paper and Hybond-ECL cut in pieces with adequate sizes were immersed in blotting buffer for pretreatment. After SDS-PAGE, a transfer apparatus was used for transferring a protein to Hybond-ECL. The resulting Hybond-ECL was subjected to blocking (in 5% skim milk) at room temperature for 1 hour and washed 3 times for 5 minutes each with Tween buffer.

For detection of TS and β-actin, the primary antibodies each diluted with Tween buffer (i.e., a mouse monoclonal anti-human TS antibody (1:1000) (ANASPEC, Inc., CA, U.S.A.) and a mouse monoclonal anti-human β-actin antibody (1:500) (Abcam, Tokyo, Japan)) were allowed to react each at 4° C. overnight. Following washing with Tween buffer 3 times for 5 minutes each, a secondary antibody (an HRP-conjugated goat anti-mouse secondary antibody (1:2000) (ICN Biomedical, CA, U.S.A.)) solution diluted with Tween buffer was allowed to react at room temperature for 1 hour. Washing with Tween buffer 3 times for 5 minutes each was followed by a reaction with an ECL chemiluminescence reagent (GE Healthcare, Little Chalfont, U.K.) for about 1 minute. The target protein band was visualized using the LAS-4000 EPUVmini (FujiFilm), photographed, and then quantified with the use of the software (Multi Gauge v.3.2, FujiFilm, Tokyo, Japan).

Figures 2, 5:
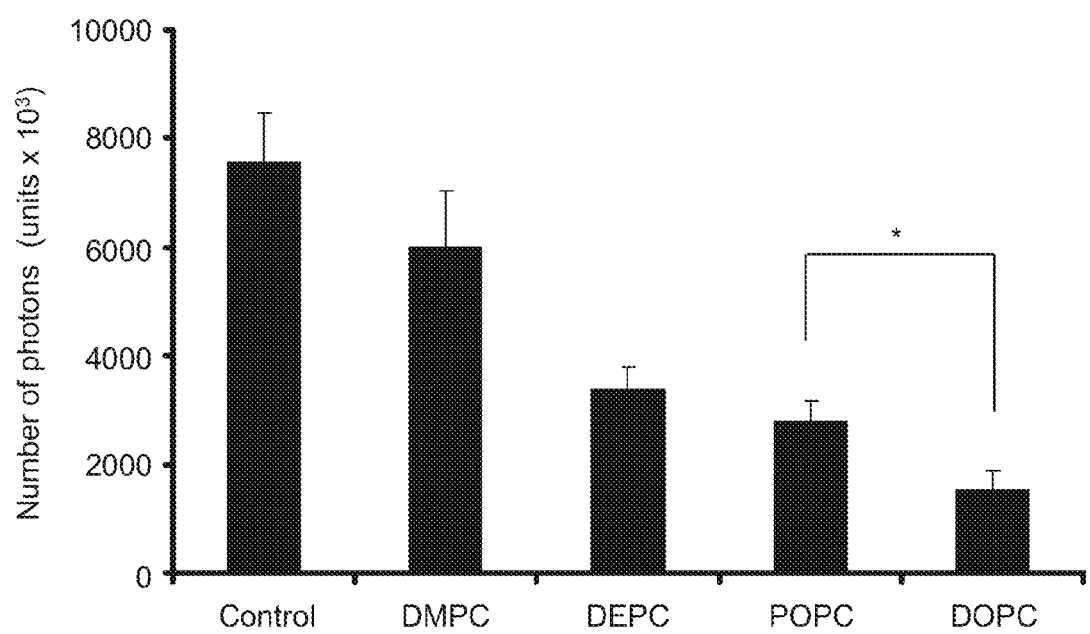

The results are shown in FIG. 2.

As shown in FIG. 2, the lipoplex having TS-shRNA bound to its outer membrane surface prepared in Example 1 was found to inhibit TS expression in the MSTO-211H cells in a sequence-specific and concentration-dependent manner to a significant extent.

Example 3

Inhibition of Luciferase Expression by Luciferase-shRNA In Vitro

Preparation of Luciferase-Expressing Cell Line

The expression plasmid into which the firefly-derived luciferase gene had been introduced (pGL3-control, Promega) and the expression plasmid into which the *Renilla reniformis*-derived luciferase gene had been introduced (pRL-TK, Promega) were subjected to transfection using Lipofectamine® 2000 (Lf 2000), which is a cationic liposome, in accordance with the manufacturer's instructions.

An HT-1080 cell suspension was seeded on a 12-well cell culture plate at 100,000 cells/well (1 ml), and culture was conducted for 12 hours in advance. After the culture supernatant was removed and washing with PBS was carried out once, a transfection solution (200 μl) containing both expression plasmids for the luciferases was added to each well, and the luciferase-expressing plasmids were subjected to transfection. The final concentration of each plasmid was adjusted to 1 μg/200 μl. After the initiation of transfection, culture was carried out at 37° C. in the presence of 5% $CO_2$.

(Preparation of Cationic Liposome)

Cationic liposomes were prepared by the method described below.

Liposome-constituting lipids were selected from among the following lipids: DOPC (1,2-dioleoyl-sn-glycero-3-phosphocholine); POPC (1-palmitoyl-2-oleoyl-sn-glycero-3-phosphocholine); DOPE (1,2-dioleoyl-sn-glycero-3-phosphoethanolamine); and DC-6-14 (O,O'-ditetradecanoyl-N-(α-trimethyl-ammonioacetyl)diethanolamine chloride). These lipids were dissolved in chloroform in advance to prepare stock solutions.

A sample was collected from each stock solution by precise measurement with the use of a glass syringe so as to achieve the following lipid composition: DOPE:X:DC-6-14=3:2:5 (molar ratio; wherein X represents DOPC or POPC). The samples were introduced into a plugged test tube and mixed therein (the total lipid amount: 200 mmol). Subsequently, chloroform was removed therefrom under a reduced pressure using a rotary evaporator (IWAKI, Tokyo), and the test tube was placed in a vacuum pump overnight, so as to completely remove chloroform. Thus, a lipid thin film was formed in the test tube. 2 ml of 9% sucrose solution (30 ml, pH 7.4) was added as an internal water phase to the lipid thin film, followed by vigorous agitation at 37° C. Thus, the lipid thin film was completely hydrolyzed such that MLVs (multilamellar vesicles) were formed (final lipid concentration: 100 mM). The obtained solution was heated to 37° C., during which LUVs (large unilamellar vesicles) having particle sizes of about 100 nm were prepared using 200-, 100-, and 50-nm polycarbonate membranes (Nucleopore, Calif., U.S.A.) by an extrusion method.

(Luciferase (Luc)-Targeting shRNA)

Luc-targeting shRNA (hereafter referred to as "Luc-shRNA") has the sequence shown below.

Luc-shRNA:
(SEQ ID NO: 12)
5'-CUUACGCUGAGUACUUCGAUAGUGCUCCUGGUUGUCGAAGUACUC
AGCGUAAGUU-3'

(Preparation of Lipoplex)

Lipoplexes were prepared by mixing the cationic liposomes with shRNAs at a rate of cationic liposome to shRNA of 800, 400, or 200:1 (molar ratio) and vigorously agitating the mixture for 10 minutes. Whether or not shRNA had completely adsorbed the cationic liposomes was inspected by confirming the absence of free shRNA via electrophoresis on 2% agarose gel.

(Inhibition of Luciferase Expression In Vitro)

Each lipoplex was added to the luciferase-expressing cells to result in the final shRNA concentration of 50 nM, and culture was carried out in a medium at 37° C. in the presence of 5% $CO_2$ for 48 hours. After the completion of culture, cell extracts were prepared and luciferase activity was assayed using the Dual Luciferase Reporter Assay System (Promega) in accordance with the manufacturer's instructions. After the completion of culture, specifically, the medium was removed, washing with cool PBS(−) was carried out, passive lysis buffer was added at 150 μl/well, and incubation was carried out at room temperature for 15 minutes with agitation with the use of a rotary shaker for cell lysis. The resultant was then transferred to sample tubes, cooled at −80° C. for 30 minutes, and then returned to room temperature. The product was centrifuged at 4° C. and 9,000×g for 30 seconds, and the resulting supernatant was used as a cell extract. Subsequently, 10 μl each of the cell extract was added to the 96-well white microplate comprising 50 μl each of the fractionated Luciferase Assay Reagent II solution, and the cells were mixed using a pipette. The microplate was mounted on the luminometer (Infinite M200 Pro, Tecan), and chemiluminescence caused by firefly luciferase activity was assayed for 10 seconds. Thereafter, the plate was removed, the Stop&Glo Reagent solution was added to the plate at 50 μl/well, and mixed via mild vortex. Immediately thereafter, chemiluminescence caused by *Renilla reniformis* luciferase activity was assayed using a luminometer in the same manner. In the analysis of the data, the *Renilla reniformis* luciferase activity level was standardized as the internal control sample, and firefly luciferase activity relative to the control group that was not subjected to shRNA was determined.

The results are shown in FIG. 3. The results shown in FIG. 3 are relative to the luciferase activity of the control designated as 100%.

As shown in FIG. 3, reduction in luciferase activity was observed with the use of either lipoplex comprising DOPC or POPC compared with the control group that was not subjected to treatment with Luc-shRNA. This indicates that the lipoplex comprising Luc-shRNA bound to its outer membrane surface is capable of inhibiting luciferase expression in HT-1080 cells. In comparison with the lipoplex comprising POPC, in addition, the lipoplex comprising DOPC was found to exhibit higher effects of inhibiting expression by Luc-shRNA. When the molar ratio of Luc-shRNA to the cationic liposome is 1:800, further, effects of inhibiting expression by Luc-shRNA were found to be high.

Example 4

Establishment of Orthotopic Implantation Mouse Models of Malignant Pleural Mesothelioma Under anesthesia with 2,2,2-tribromoethanol (Avertin; Sigma-Aldrich), 100 μl of a suspension of MSTO-211H cells (MSTO-211H-Luc cells) stably expressing luciferase was implanted into the left pleural cavity of a nude mouse (5-week-old male). Under anesthesia with isoflurane, 100 μl of a D-luciferin potassium salt (Wako Pure Chemical) solution (7.5 mg/ml) was intraperitoneally administered 3, 7, 14, and 21 days after the implantation of the cells, and the bioluminescence levels depending on activity of the MSTO-211H-Luc cells that had grown in the thoracic cavity were evaluated using IVIS (Xenogen, Alameda, Calif., U.S.A.).

Figure 4:
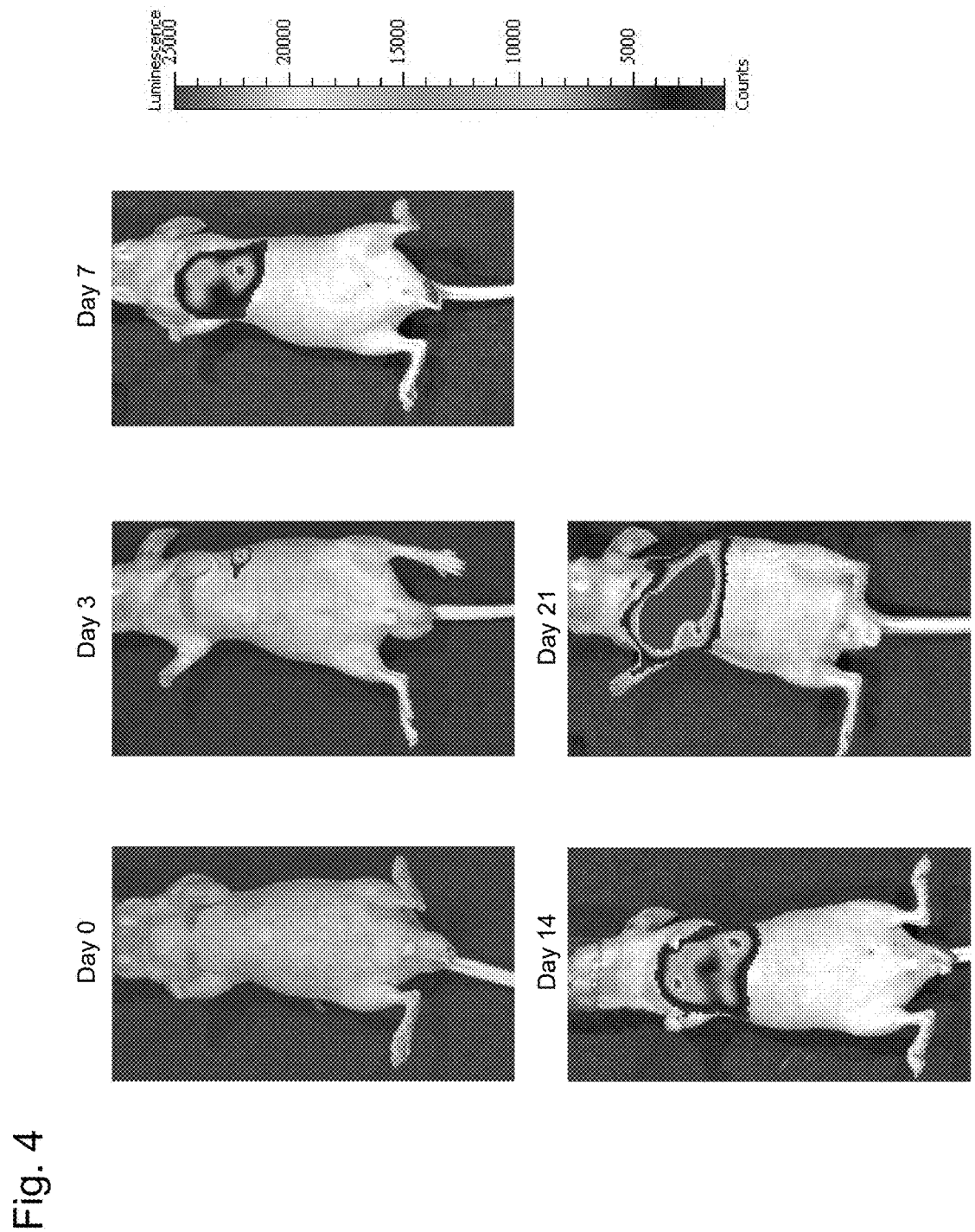
FIG. 4 shows photographs demonstrating the results of tumor growth in orthotopic implantation mouse models of malignant pleural mesothelioma. The number of days indicated for each photograph represents the number of days after implantation of malignant pleural mesothelioma cells.

The results are shown in FIG. 4.

As shown in FIG. 4, insignificant bioluminescence was observed upon the growth of the MSTO-211H-Luc cells 3 days after implantation, and bioluminescence was then enhanced with the elapse of time. This indicates that the implanted MSTO-211H-Luc cells were sufficiently grown in the thoracic cavity. Thus, the orthotopic implantation mouse models of malignant pleural mesothelioma were established.

Example 5

Selection of Cationic Liposome Exhibiting Sufficient Effects of shRNA Introduction in Vivo (Preparation of Cationic Liposome)

Cationic liposomes were prepared by the method described below.

Liposome-constituting lipids were selected from among the following lipids: DOPC (1,2-dioleoyl-sn-glycero-3-phosphocholine); POPC (1-palmitoyl-2-oleoyl-sn-glycero-3-phosphocholine); DMPC (1,2-dimyristoyl-sn-glycero-3-phosphorylcholine); DEPC (1,2-dierucoyl-sn-glycero-3-phosphocholine); DOPE (1,2-dioleoyl-sn-glycero-3-phosphoethanolamine); and DC-6-14 (O,O'-ditetradecanoyl-N-(α-trimethyl-ammonioacetyl) diethanolamine chloride). These lipids were dissolved in chloroform in advance to prepare stock solutions.

A sample was collected from each stock solution by precise measurement with the use of a glass syringe so as to achieve the following lipid composition: DOPE:X:DC-6-14=3:2:5 (molar ratio), and cationic liposomes were prepared in accordance with the method described in Example 3. The particle sizes (the dynamic light scattering method) and the zeta potentials (the electrophoresis light scattering method) of the liposomes were determined using an NICOMP 370 (Particle Sizing System, CA, U.S.A.). The surface charges of the liposomes were about +50 mV.

(Luciferase (Luc)-Targeting shRNA)

Luc-shRNA described in Example 3 was used.

(Preparation of Lipoplex)

Lipoplexes were prepared by mixing the cationic liposomes with shRNAs at a ratio of 2000:1 (molar ratio) and vigorously agitating the mixture for 10 minutes. Whether or not shRNAs had completely adsorbed to the cationic liposomes was inspected by confirming the absence of free shRNA via electrophoresis on 2% agarose gel.

The average particle size and the zeta potential of the prepared liposomes were about 350 nm and about +15 mV, respectively.

(Inhibition of Luciferase Expression Using Orthotopic Implantation Mouse Models In Vivo)

Under anesthesia with 2,2,2-tribromoethanol (Avertin; Sigma-Aldrich), 100 μl of a suspension of MSTO-21111 cells (MSTO-211H-Luc cells) stably expressing luciferase was implanted into the left pleural cavity of a nude mouse (5-week-old male). The lipoplex was administered directly into the thoracic cavity 10, 13, 16, and 19 days after the cell implantation, so that 20 μg (50 μl) of shRNA would be administered. Under anesthesia with isoflurane, 100 μl of a D-luciferin potassium salt solution (7.5 mg/ml) was intraperitoneally administered 2 days after the final administration of the lipoplex, and the bioluminescence levels depending on activity of the MSTO-211H-Luc cells that had grown in the thoracic cavity were evaluated using IVIS (Xenogen, Alameda, Calif., U.S.A.).

A 9% sucrose solution was administered to the control.

The results are shown in FIG. 5-1 and FIG. 5-2.

As shown in FIG. 5-1 and FIG. 5-2, it was found that the degree of inhibition of luciferase expression would be influenced by the lipid composition of the cationic liposome used and that the lipoplex prepared with the use of the cationic liposome with the lipid composition of DOPE/DOPC/DC-6-14 (3:2:5) would inhibit luciferase expression in the MSTO-211H-Luc cells that had been implanted into the thoracic cavity, to the greatest extent.

Example 6

Influence of Positively-Charged Lipid (DC-6-14 Content) Upon shRNA Introduction in Vivo (Preparation of Cationic Liposome)

Liposomes were prepared in accordance with the method described in Example 3; however, the lipid composition of the liposomes was adjusted to DOPE:POPC:DC-6-14 of 3:2+X:5−X (molar ratio, wherein X is 0, 1.5, or 3.0). The particle sizes and the surface charges of the liposomes were determined using an NICOMP 370 (Particle Sizing System, CA, U.S.A.). All the LUVs (large unilamellar vesicles) were confirmed to have particle sizes of about 100 nm. The surface charge of a liposome containing DC-6-14 at 20% was found to be about +25 mV, that of the liposome containing DC-6-14 at 35% was found to be about +35 mV, and that of the liposome containing DC-6-14 at 50% was found to be about +50 mV.

(Preparation of Lipoplex)

Lipoplexes were prepared by mixing the Luc-shRNAs described in Example 3 with liposomes by the method described in Example 3. The particle sizes (the dynamic light scattering method) and the zeta potentials (the electrophoresis light scattering method) of the liposomes were determined using an NICOMP 370 (Particle Sizing System, CA, U.S.A.). The particle size and the surface charge of the lipoplex containing DC-6-14 at 20% were about 350 nm and about +25 mV, respectively. The particle size and the surface charge of the lipoplex containing DC-6-14 at 35% were about 350 nm and about +30 mV, respectively. The particle size and the surface charge of the lipoplex containing DC-6-14 at 50% were about 350 nm and about +35 mV, respectively.

(Inhibition of Luciferase Expression Using Orthotopic Implantation Mouse Models In Vivo)

In accordance with the method described in Example 5, effects of the prepared lipoplexes for inhibiting gene expression in vivo (the efficiency for shRNA introduction into cells) were evaluated.

Figures 2, 6:
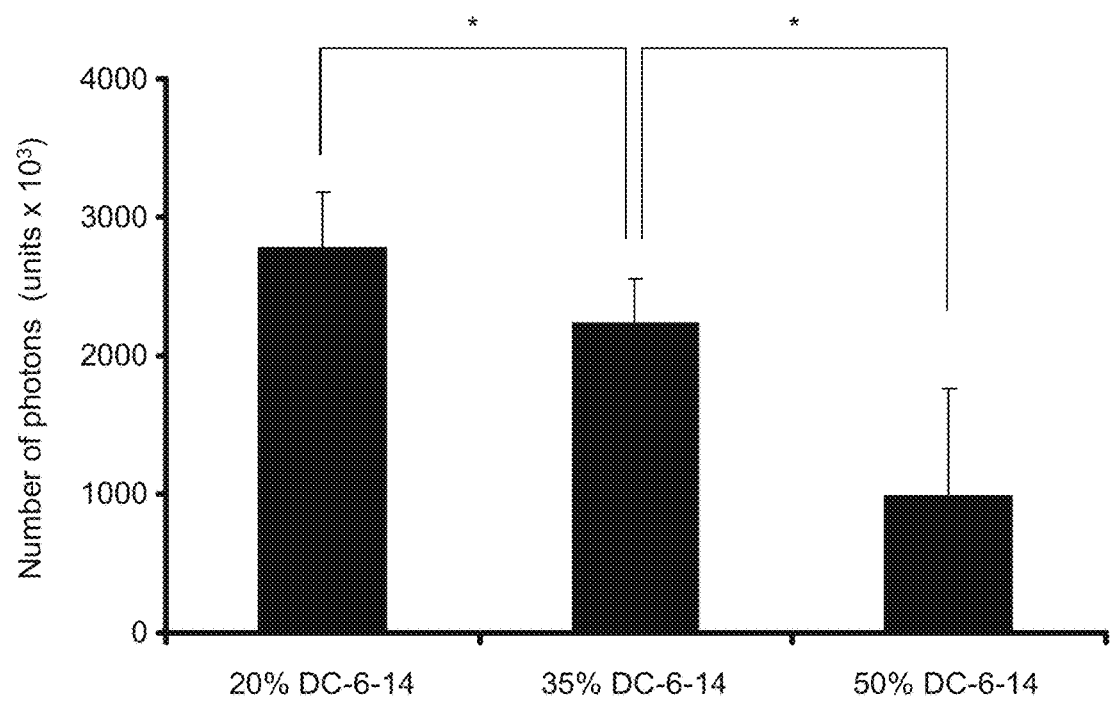

The results are shown in FIG. 6-1 and FIG. 6-2.

As shown in FIG. 6-1 and FIG. 6-2, it was found that inhibitory effects of the lipoplex on luciferase expression would be enhanced in vivo as the amount of positively-charged lipid (DC-6-14) was increased in the liposome. An increased surface charge is advantageous when forming a complex of a liposome with a negatively-charged shRNA. In addition, interactions with negatively-charged tumor cells would be facilitated because of an increased surface charge. As a result, a large amount of shRNA can be efficiently introduced into cells.

Example 7

Influence of PEG Modification on shRNA Introduction In Vivo (Preparation of PEG-Modified Cationic Liposome)

Liposomes were prepared in accordance with the method described in Example 3.

Liposome-constituting lipids were selected from among the following lipids: DOPC, POPC, DOPE, DC-6-14, and 1,2-distearoyl-sn-glycero-3-phosphoethanolamine-N-[methoxy(polyethylene glycol)-2000] (mPEG2000-DSPE). The lipid composition of the PEG-modified liposome was adjusted to DOPE:X:DC-6-14:mPEG-DSPE=3:2:5:0.1 (molar ratio, wherein X represents DOPC or POPC), the lipid composition of the non-PEG-modified liposome was adjusted to DOPE:X:DC-6-14 of 3:2:5 (molar ratio, wherein X represents DOPC or POPC), and the LUVs (large unilamellar vesicles) were then prepared. The particle sizes of the liposomes were determined using NICOMP 370 (Particle Sizing System, CA, U.S.A.). The particle size and the surface charge of the liposome containing DOPC (the non-PEG-modified liposome) were about 100 nm and about +50 mV, respectively. The particle size and the surface charge of the liposome containing POPC (the non-PEG-modified liposome) were about 110 nm and about +50 mV, respectively. The particle size and the surface charge of the PEG-modified liposome containing DOPC (the PEG-modified liposome) were about 106 nm and about +50 mV, respectively. The particle size and the surface charge of the PEG-modified liposome containing POPC (the PEG-modified liposome) were about 100 nm and about +50 mV, respectively.

(Preparation of Lipoplex)

Lipoplexes were prepared by mixing the Luc-shRNAs described in Example 3 with the PEG-modified liposomes or non-PEG-modified liposomes by the method described in Example 3. The particle sizes (the dynamic light scattering method) and the zeta potentials (the electrophoresis light scattering method) of the lipoplexes were determined using an NICOMP 370 (Particle Sizing System, CA, U.S.A.). The particle size and the surface charge of the lipoplex containing DOPC were about 350 nm and about +30 mV, respectively. The particle size and the surface charge of the lipoplex containing POPC were about 360 nm and about +30 mV, respectively. The particle size and the surface charge of the PEG-modified lipoplex containing DOPC were about 370 nm and about +30 mV, respectively. The particle size and the surface charge of the PEG-modified lipoplex containing POPC were about 370 nm and about +30 mV, respectively.

(Inhibition of Luciferase Expression Using Orthotopic Implantation Mouse Models In Vivo)

In accordance with the method described in Example 5, effects of the prepared PEG-modified lipoplex or non-PEG-modified lipoplex for inhibiting gene expression in vivo (the efficiency for shRNA introduction into cells) were evaluated.

Figures 2, 7:
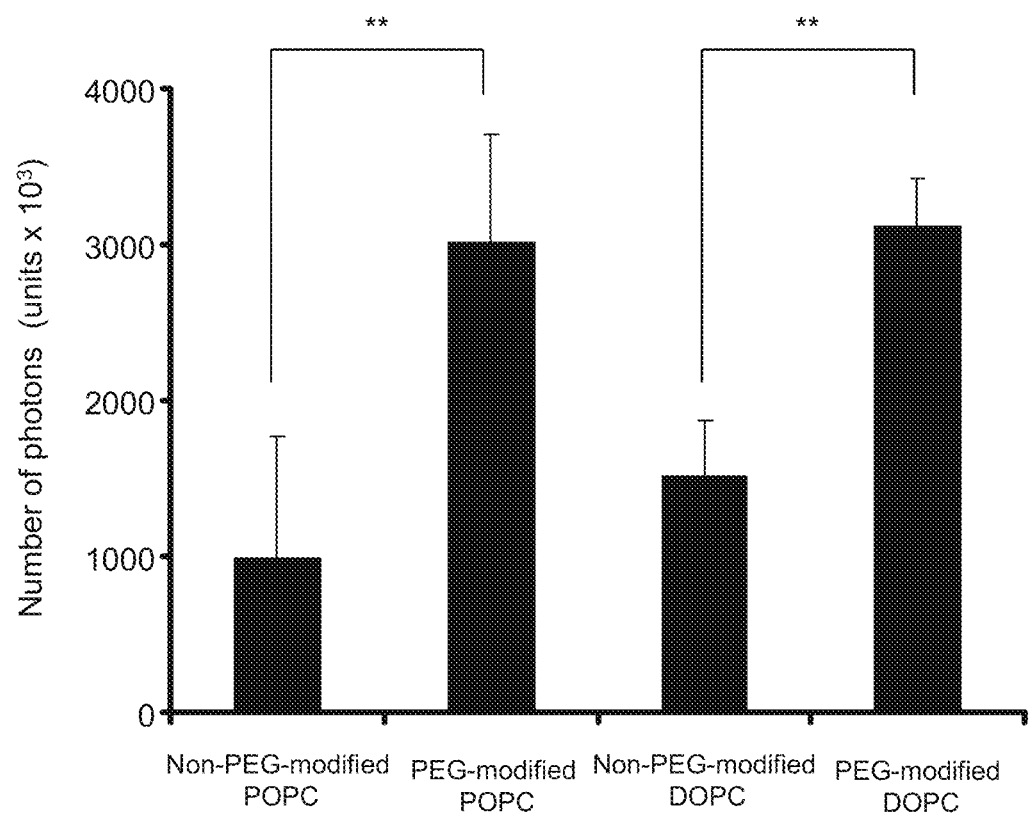

The results are shown in FIG. 7-1 and FIG. 7-2.

As shown in FIG. 7-1 and FIG. 7-2, it was found that inhibitory effects of the lipoplex on luciferase expression would be inhibited through PEG-modification, regardless of the lipid composition of the cationic liposome used. While PEGylation was necessary in the case of intravenous administration, it was found that PEG-modification would deteriorate the efficiency for shRNA introduction into cells in the case of intrathoracic administration Example 8

Effects of tumor growth inhibition via intrathoracic administration of lipoplex having TS-shRNA bound to its outer membrane surface in orthotopic implantation mouse models of malignant pleural mesothelioma (Establishment of Orthotopic Implantation Mouse Models of Malignant Pleural Mesothelioma)

Orthotopic implantation mouse models of malignant pleural mesothelioma using the MSTO-211H-Luc cells were prepared by the method described in Example 3, and mice in which implanted cells had been sufficiently fixed 7 days after implantation were subjected to in vivo experiment.

(Preparation of Cationic Liposome)

Liposomes were prepared in accordance with the method described in Example 3; however, the lipid composition of the liposomes was adjusted to DOPE:POPC:DC-6-14 of 3:2:5.

(Preparation of Lipoplex)

Lipoplexes were prepared by mixing the shRNAs described in Example 1 with the liposomes by the method described in Example 3. The particle sizes (the dynamic light scattering method) and the zeta potentials (the electrophoresis light scattering method) of the lipoplexs were determined using an NICOMP 370 (Particle Sizing System, CA, U.S.A.). The particle size of the lipoplex having TS-shRNA bound to its outer membrane surface (hereafter, referred to as "TS-shRNA lipoplex") was about 400 nm, and the surface charge thereof was about +30 mV. In contrast, the particle size of the lipoplex having NS-shRNA bound to its outer membrane surface (hereafter, referred to as "NS-shRNA lipoplex") was about 400 nm, and the surface charge thereof were about +30 mV.

(Evaluation of Effects of TS-shRNA Lipoplex on Tumor Growth Inhibition)

The TS-shRNA lipoplex or NS-shRNA lipoplex was directly administered into the thoracic cavity of a mouse carrying MSTO-211H-Luc cells every other day from 7 days to 17 days after the tumor implantation, and administration was carried out 6 times in total. A dose was 20 µg of shRNA/100 µl.

When an existing cancer chemotherapeutic agent (Alimta; pemetrexed sodium hydrate (PMX), Eli Lilly) was used in combination, a dose of 25 mg/kg was intraperitoneally administered every day from 7 days to 11 days after the tumor implantation, the same amount of the agent was intraperitoneally administered after an interval of 2 days every day from 14 days to 18 days after the tumor implantation, and administration was carried out 10 times in total. A 9% sucrose solution was administered to the control.

As described in Example 5, carcinostatic activity (i.e., cell growth inhibitory activity) was evaluated by implanting MSTO-211H-Luc cells, administering 100 µl of a D-luciferin potassium salt solution (7.5 mg/ml) intraperitoneally under anesthesia with isoflurane 21 days after implantation, and evaluating the bioluminescence levels depending on activity of the MSTO-211H-Luc cells that had grown in the thoracic cavity using IVIS (Xenogen, Alameda, Calif., U.S.A.).

Life-prolonging effects on the basis of carcinostatic effects were evaluated by continuously breeding mouse models that had been subjected to the IVIS-based evaluation up to 47 days after the cell implantation without treatment.

The mean survival times (MST; the number of days) were evaluated on the basis of the following equation.

MST (the number of days)=the day on which the first mouse died+the day on which the last mouse died/2

The increased life span (%) was determined in accordance with the following formula:

ILS (%)=[mean survival time for treatment group/ mean survival time for control group]×100

The results are shown in FIGS. 8-1, 8-2, 8-3, and 8-4.

Figures 1, 8:
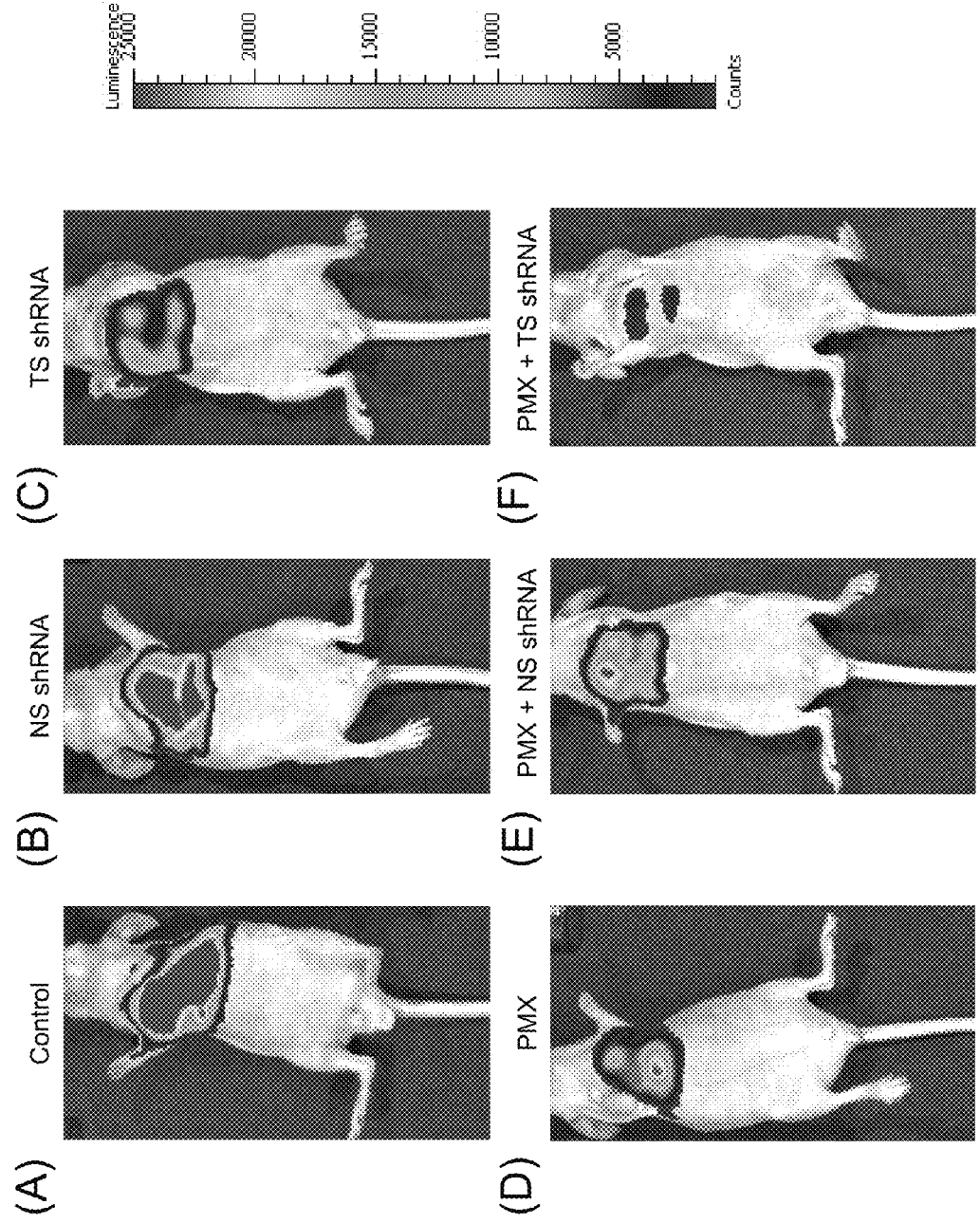
Figures 2, 8:
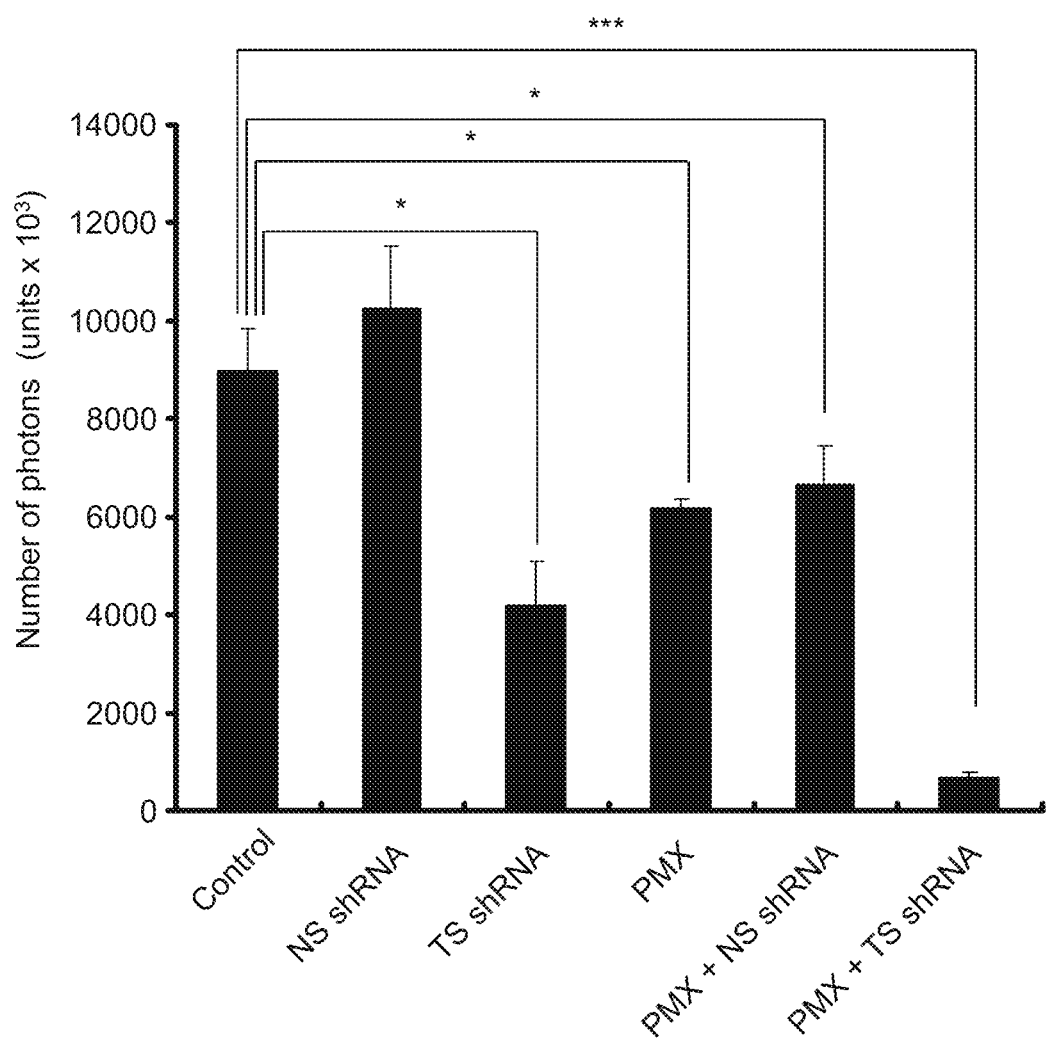
Figures 3, 8:
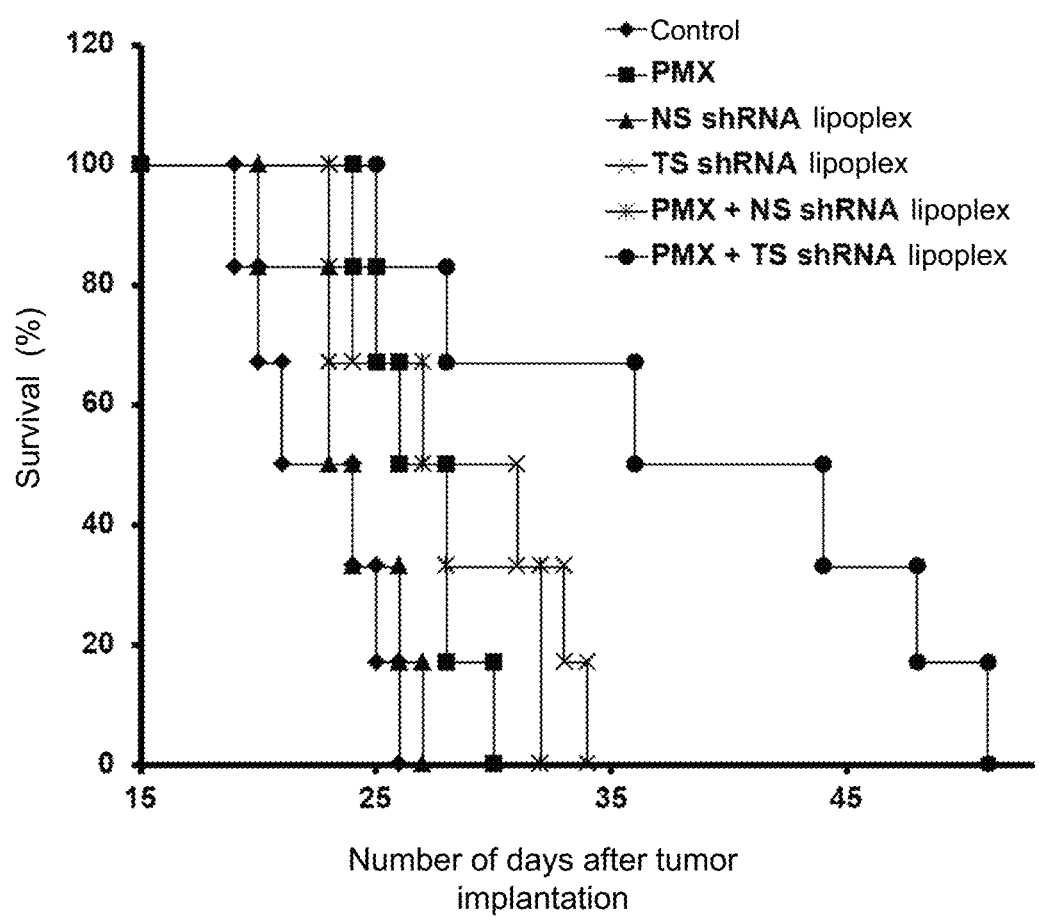

As shown in FIGS. 8-1 and 8-2, tumor growth inhibitory effects were not observed in the group subjected to treatment with the NS-shRNA lipoplex alone compared with the control group. In contrast, about 50% of tumor growth inhibitory effects were observed in the group subjected to treatment with the TS-shRNA lipoplex or PMX alone. In addition, tumor growth inhibitory effects substantially the same as those observed in the group subjected to treatment with PMX alone were observed in the group subjected to treatment with the NS-shRNA lipoplex in combination with PMX. However, significant tumor growth inhibitory effects as high as about 90% were observed in the group subjected to treatment with the TS-shRNA lipoplex in combination with PMX.

As shown in FIGS. 8-3 and 8-4, substantially no life-prolonging effects were observed in the group subjected to treatment with the NS-shRNA lipoplex alone compared with the control group. In contrast, insignificant life-prolonging effects (120% to 126%) were observed in the group subjected to treatment with the TS-shRAN lipoplex or PMX alone. In addition, life-prolonging effects (122%) substantially the same as those observed in the group subjected to treatment with PMX alone were observed in the group subjected to treatment with the NS-shRNA lipoplex in combination with PMX. However, the maximal life-prolonging effects (178%) reflecting the tumor growth inhibitory effects were observed in the group subjected to treatment with the TS-shRNA lipoplex in combination with PMX.

Serious toxicity, including weight increase inhibition, was not observed in any treatment groups.

Example 9

Examination of Inhibition of Target Gene Expression Via Intrathoracic Administration of TS-shRNA Lipoplex Mice of the groups subjected to the treatment in the same manner as in Example 8 were subjected to evaluation via IVIS 21 days after the implantation of the MSTO-211H-Luc cells, mice were sacrificed, tumor cells were collected from the thoracic cavity, and the inhibition of TS gene expression in the collected tumor cells was evaluated via quantitative RT-PCR.

RNA was extracted from tumor cells using the RNaqueous-micro kit (Ambion, Austin, Tex., U.S.A.) in accordance with the method recommended by the manufacturer. Reverse transcription of RNA into cDNA was carried out with the addition of Oligo (dT)20, dNTP, RNase inhibitor, and ReverTra Ace (Toyobo, Osaka, Japan) to RNA. Real-time PCR was carried out using the StepOnePlus real-time PCR system (Applied Biosystems, CA, U.S.A.), the reversely-transcribed cDNA as the template, and FastStart TaqMan Probe Master (ROX) and Universal ProbeLibrary (Roche Diagnostics GmbH, Manheim, Germany) as reagents, in accordance with the method recommended by the manufacturer. GAPDH was used as the internal standard.

Figure 9:
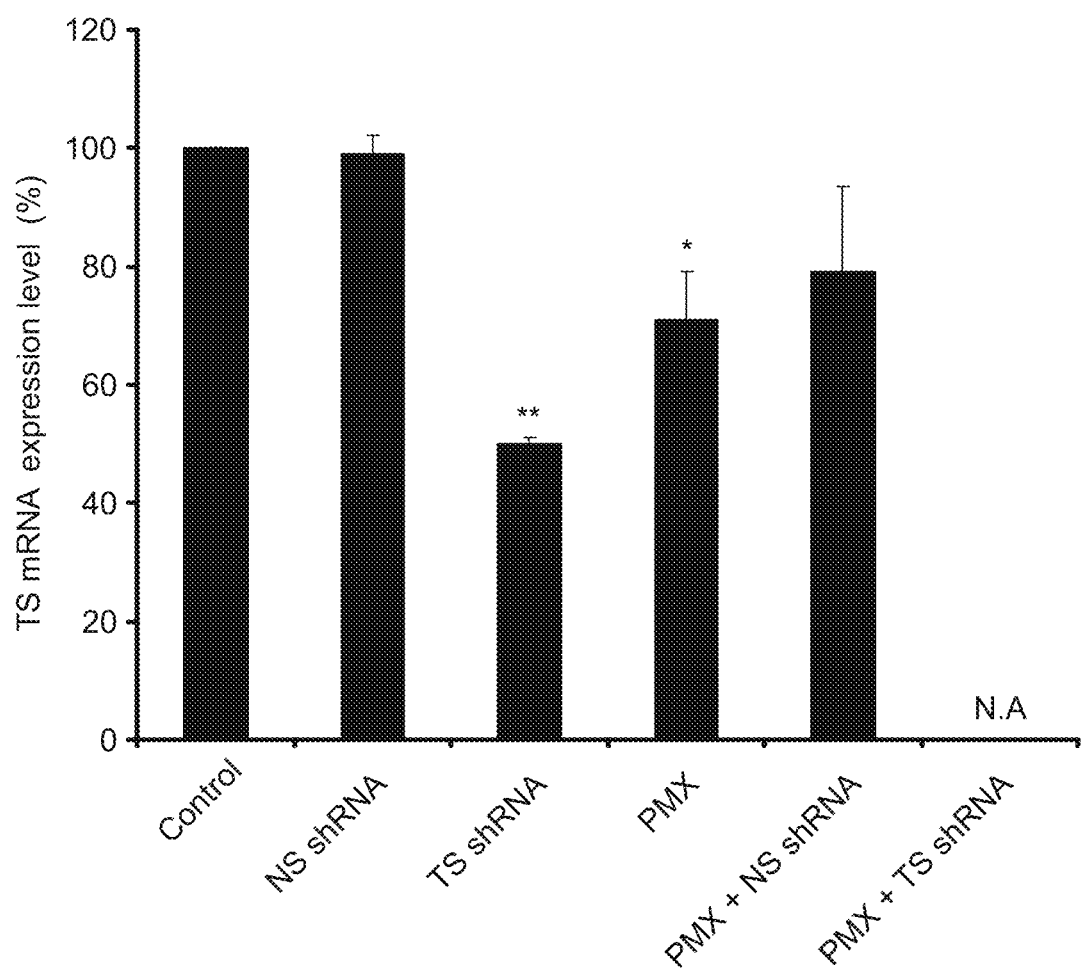
FIG. 9 shows the results of quantification of TS mRNA expression levels in tumor cells of orthotopic implantation mouse models of malignant pleural mesothelioma subjected to treatment with the control (9% sucrose), a lipoplex comprising NS-shRNA bound to its outer membrane surface alone, a lipoplex having TS-shRNA bound to its outer membrane surface alone, a cancer chemotherapeutic agent (PMX) alone, or a lipoplex in combination with a cancer chemotherapeutic agent (PMX). TS mRNA expression levels are represented in percentage form relative to 100%, which is assigned to the control (*: $p<0.05$; **: $p<0.01$).

The results are shown in FIG. 9.

As shown in FIG. 9, no inhibitory effects were observed on the TS gene in the group subjected to treatment with the NS-shRNA lipoplex alone compared with the control group. In contrast, about 50% or about 25% of TS gene inhibitory effects were observed in the group subjected to treatment with the TS-shRNA lipoplex or PMX alone. In addition, about 20% of TS gene inhibitory effects, which were substantially the same as those observed in the group subjected to treatment with PMX alone, were observed in the group subjected to treatment with the NS-shRNA lipoplex in combination with PMX. In the group subjected to treatment with the TS-shRNA lipoplex in combination with PMX that had exhibited the highest tumor growth inhibitory effects in Example 8, substantially no tumor cells remained in the thoracic cavity because of high inhibitory effects. Accordingly, it was not possible to measure changes in TS gene expression.

Example 10

Influence of Configuration of Lipid Mixture on shRNA Introduction In Vitro Preparation of Cationic Presome The lipid composition employed in Example 3; that is, DOPE:X:DC-6-14=3:2:5 (X represents DOPC or POPC), was employed herein.

Lipids were measured so as to achieve the lipid composition described above, and cyclohexane in an amount 10 times the amount of the total lipid by weight and ethanol in an amount of 2% of cyclohexane by weight were added to lyse the lipids in warm water at 70° C. The lysate was filtered through a 0.2-μm PTFE membrane filter, and the filtered solution was frozen with dry ice/acetone. After the completion of freezing, vacuum drying was carried out for 12 hours or longer with the use of a vacuum pump. Thus, cationic presomes were obtained.

A solution of cationic presomes used in the experiment was prepared by adding a 9% sucrose solution (pH 7.4) to the cationic presomes obtained by the method described above, so as to adjust the final lipid concentration to 100 mM, and vigorously agitating the mixture for 10 minutes. The average particle size of the cationic presomes was about 440±210 nm (mean±standard deviation).

Preparation of Lipoplex and Preplex

Lipoplexes and preplexes were prepared using the cationic liposomes described in Example 3 and the cationic presomes described above, respectively. The luciferase-targeting Luc-shRNA described in Example 3 were equipped with the lipoplexes and the preplexes.

The cationic liposomes or cationic presomes were mixed with Luc-shRNAs at a ratio of 1600:1 or 800:1 by mole, and the resultants were vigorously agitated for 10 minutes. Thus, the lipoplexes and the preplexes having Luc-shRNA bound to its outer membrane surface were prepared.

Transfection into HT-1080 Cells

As a transfection reagent, Lipofectamine™ 2000 (hereafter referred to as "Lf2000"), which is a cationic liposome, was used. As firefly-derived and sea slug-derived luciferase expressing plasmids, pGL3-C and pRL-TK (Promega) were used.

The firefly-derived and sea slug-derived luciferase expressing plasmids (15 μg+15 μg) and 30 μl of Lf2000 were separately diluted with OptiMEM to prepare 750 μl of the solutions thereof, the resulting solutions were mixed, the mixture was allowed to stand at room temperature for 10 to 20 minutes to form a Luc-lipoplex.

A suspension of human fibrosarcoma cells (HT-1080) (10,000 cells/ml) was seeded on a 12-well plate, the culture solution was removed therefrom 24 hours thereafter, 100 μl of the Luc-lipoplex was added thereto, and culture was then conducted at 37° C. in the presence of 5% $CO_2$ for 5 hours.

Thereafter, the culture solution was removed, the plate was washed with cool PBS(–) once, 100 μl of a solution of a lipoplex having Luc-shRNA bound to its outer membrane surface or a solution of a preplex having Luc-shRNA bound to its outer membrane surface (the final shRNA concentration in each well was 50 nM) was added in combination with 900 μl of a fresh DMEM medium, and culture was then conducted at 37° C. in the presence of 5% $CO_2$ for an additional 48 hours.

Luciferase Activity Assay

Luciferase activity assay was carried out with the use of the Dual-Luciferase Reporter Assay System (Promega) and a 96-well microplate. Culture was conducted for 48 hours, the medium was removed, the plate was washed with cool PBS(–) once, and 150 μl of passive lysis buffer was directly added to the wells for cell lysis. Freeze-thawing was carried out once, centrifugation was carried out at 10,000×g and 4° C. for 30 seconds, and the resulting supernatant was used as a cell extract.

The Luciferase Assay Reagent II (50 μl) and 10 μl of the cell extract were added to each well, and the bioluminescence level was assayed on the basis of the firefly luciferase activity with the use of a microplate reader (Infinite 200® Pro, Tecan). Thereafter, 50 μl of the Stop & Glo® Reagent was further added, and sea slug luciferase activity was assayed in the same manner.

Firefly-derived luciferase activity was determined in accordance with the formula shown below, relative to the activity without Luc-shRNA treatment.

Firefly-derived luciferase relative activity (%)=(firefly luciferase activity/sea slug luciferase activity)/(firefly luciferase activity without Luc-shRNA treatment/sea slug luciferase activity without Luc-shRNA treatment)×100

Figure 10:
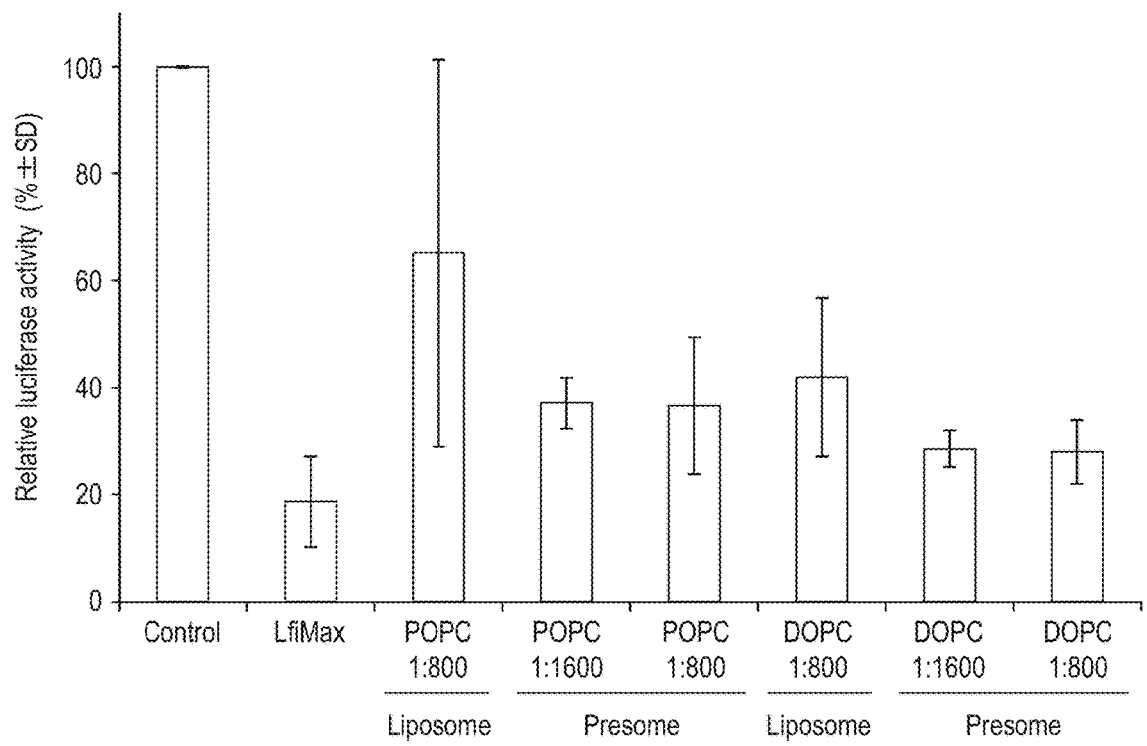
FIG. 10 shows the results of a comparison of effects of Luc-shRNA introduction with the use of various cationic liposomes and cationic presomes via dual-luciferase assays.

The results are shown in FIG. 10.

As shown in FIG. 10, luciferase expression was more efficiently inhibited with a preplex having Luc-shRNA bound to its outer membrane surface, compared with a lipoplex having Luc-shRNA bound to its outer membrane surface. Whether the complex contained DOPC or POPC was not significant. Also, a preplex containing DOPC exhibited somewhat higher efficiency for expression inhibition than a preplex containing POPC in the group to which the preplex had been administered.

Example 11

Tumor Growth Inhibitory Effects Achieved by Intrathoracic Administration of Lipoplex and Preplex Each Having TS-shRNA Bound to its Outer Membrane Surface in Orthotopic Implantation Models of Malignant Pleural Mesothelioma Establishment of Orthotopic Implantation Models of Malignant Pleural Mesothelioma Orthotopic implantation models of malignant pleural mesothelioma using the MSTO-211H-Luc cells were prepared by the method described in Example 4, and the mice 4 days after implantation were subjected to the in vivo experiment.

Preparation of Lipoplex and Preplex Each Having TS-shRNA Bound to its Outer Membrane Surface In accordance with the method described in Example 10, cationic liposomes and cationic presomes with the lipid composition of DOPE:DOPC:DC-6-14 of 3:2:5 were prepared. The liposomes and the presomes were mixed with the TS-targeting shRNA described in Example 1 to prepare a lipoplex (a TS-lipoplex) and a preplex (a TS-preplex). The ratio of the liposomes or presomes to shRNAs was 2000:1 by mole. The average particle size of the TS-liposome and that of the TS-preplex prepared were about 210±100 nm and about 630±400 nm (mean±standard deviation), respectively.

Evaluation of tumor growth inhibitory effects on the preplex and the lipoplex each having TS-shRNA bound to its outer membrane surface.

The TS-lipoplex or TS-preplex was administered directly into the thoracic cavity 4, 7, 10, 13, and 16 days after the tumor implantation, so that 20 µg (50 µl) of shRNA would be administered.

When an existing chemotherapeutic agent (Alimta; pemetrexed sodium hydrate (PMX), Eli Lilly) was used in combination, a dose of 25 mg/kg was intraperitoneally administered every day from 4 days to 8 days after the tumor implantation, the same amount of the agent was intraperitoneally administered after an interval of 2 days every day from 11 days to 15 days after the tumor implantation, and administration was carried out 10 times in total.

Two days after the final administration of the TS-lipoplex or TS-preplex (i.e., 18 days after the tumor implantation), 100 µl of a D-luciferin potassium salt solution (7.5 mg/ml) was administered intraperitoneally under anesthesia with isoflurane, and the bioluminescence levels depending on luciferase activity in the MSTO-211H-Luc cells that had grown in the thoracic cavity were evaluated using IVIS (Xenogen, Alameda, Calif., U.S.A.).

Figure 11:
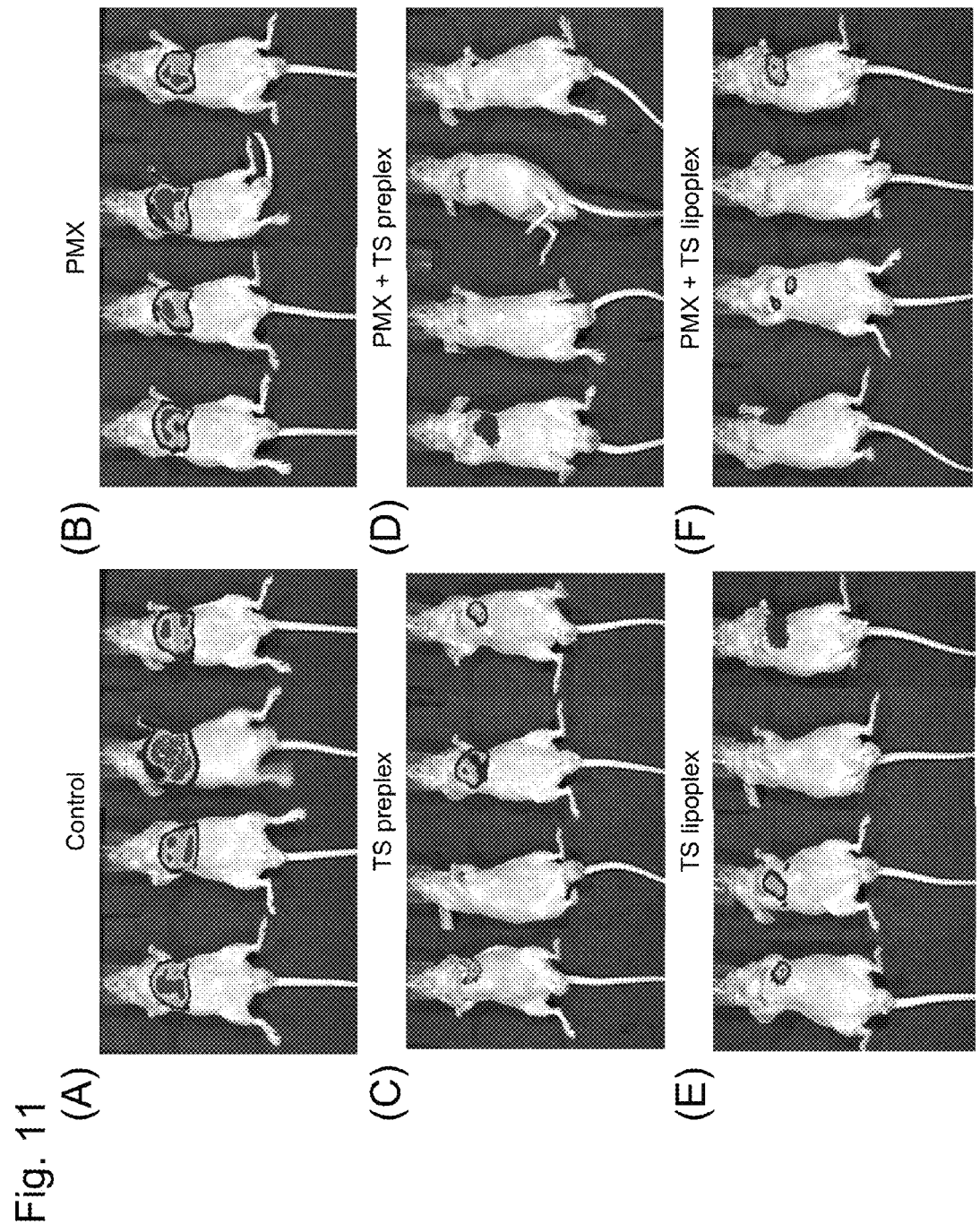
FIG. 11 shows photographs demonstrating the results of a comparison of the tumor growth inhibitory effects of a lipoplex having TS-shRNA bound to its outer membrane surface, a preplex having TS-shRNA bound to its outer membrane surface, a cancer chemotherapeutic agent (PMX), and a lipoplex or preplex in combination with a cancer chemotherapeutic agent (PMX) on tumor cells in orthotopic implantation mouse models of malignant pleural mesothelioma.

The results are shown in FIG. 11.

Tumor growth inhibitory effects observed in the group subjected to treatment with PMX alone were insignificant, in comparison with the control group without treatment. In the group subjected to treatment with the TS-lipoplex or TS-preplex alone, in contrast, tumor growth inhibitory effects were apparently higher, compared with the control group and the group subjected to treatment with PMX alone. While the highest tumor growth inhibitory effects were observed in the group subjected to treatment with the TS-lipoplex or TS-preplex in combination with PMX, no significant differences were observed between the effects attained with the lipoplex and the effects attained with the preplex.

Figure 12:
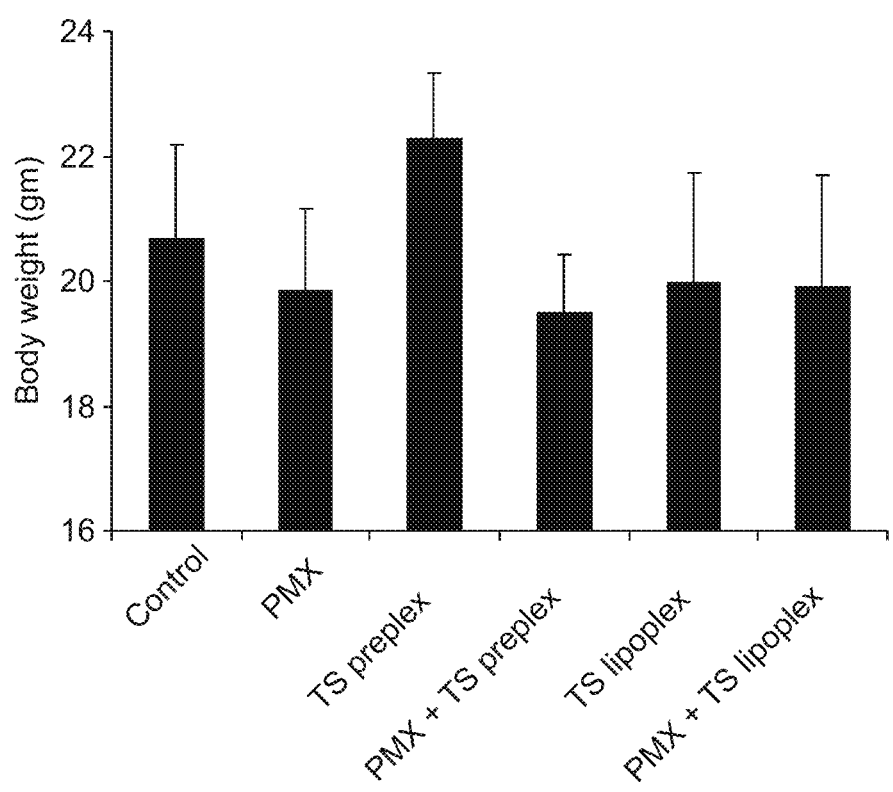
FIG. 12 shows the results of measurements of body weights of orthotopic implantation mouse models of malignant pleural mesothelioma subjected to treatment with a cancer chemotherapeutic agent and/or a lipoplex or preplex having TS-shRNA bound to its outer membrane surface.

FIG. 12 shows the results of measurement of body weights of mice when subjected to the evaluation via IVIS, and no statistically significant differences were observed in any groups. This indicates that the method of administration employed herein does not have serious toxicity.

INDUSTRIAL APPLICABILITY

Topical administration of the liposome according to the present invention having an active ingredient thereon enables efficient delivery of an active ingredient to limited cells in the target site of administration and/or the vicinity thereof. In addition, topical administration of the liposome according to the present invention having, as an active ingredient, an RNAi molecule capable of inhibiting the tumor growth to the tumor and/or an area in the vicinity thereof enables efficient delivery of an RNAi molecule to the target tumor cell. Thus, the tumor growth can be efficiently inhibited. The present invention is expected to make a significant contribution in the field of drug delivery or cancer treatment.

All publications, patents, and patent applications cited herein are incorporated herein by reference in their entirety.

The invention claimed is:

1. A liposome for topical administration consisting of:
dioleylphosphatidylethanolamine (DOPE);
a phosphatidylcholine comprising at least one unsaturated fatty acid chain containing a carbon-to-carbon double bond; and
O,O'-ditetradecanoyl-N-(α-trimethylammonioacetyl)diethanolamine chloride (DC-6-14).

2. The liposome according to claim 1, wherein the phosphatidylcholine comprises at least one unsaturated fatty acid chain containing a cis-form carbon-to-carbon double bond.

3. The liposome according to claim 1, wherein the phosphatidylcholine is 1,2-dioleoyl-sn-glycero-3-phosphocholine (DOPC), palmitoyl-oleoyl phosphatidylcholine (POPC), or 1,2-dieicosenoyl-sn-glycero-3-phosphocholine (DEPC).

4. The liposome according to claim 1, which consists of DOPE, DOPC, and DC-6-14.

5. The liposome according to claim 4, wherein DOPE, DOPC, and DC-6-14 are present in a molar ratio of 3:2:5 by mole.

6. A composition comprising the liposome according to claim 1 and an active compound which is DNA, RNA, a DNA-RNA hybrid, a protein, or a peptide.

7. The composition according to claim 6, wherein the active compound is a nucleic acid.

8. The composition according to claim 7, wherein the nucleic acid is bound to the outer membrane surface of the liposome.

9. An antitumor agent comprising the liposome according to claim 1 and short hairpin RNA (shRNA) capable of inhibiting thymidylate synthase expression via RNAi.

10. The antitumor agent according to claim 9, wherein the shRNA is bound to the outer membrane surface of the liposome.

11. The antitumor agent according to claim 9, wherein the shRNA consists of the nucleotide sequence as shown in SEQ ID NO: 8.

12. A method of treating cancer, the method comprising treating a patient in need thereof with the antitumor agent according to claim 9, in combination with cancer chemotherapy or in combination with a cancer chemotherapeutic agent.

13. A combined product comprising the antitumor agent according to claim 9 and a cancer chemotherapeutic agent.

14. The combined product according to claim 13, wherein the cancer chemotherapeutic agent is an antitumor agent having TS inhibitory action.

15. The combined product according to claim 14, wherein the antitumor agent having TS inhibitory action is a 5-FU antitumor agent or pemetrexed sodium hydrate.

* * * * *

SEQUENCE LISTING

```
<160> NUMBER OF SEQ ID NOS: 12

<210> SEQ ID NO 1
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 1
guaacaccau cgaucauga                                              19

<210> SEQ ID NO 2
<211> LENGTH: 19
<212> TYPE: RNA
<213> ORGANISM: Artificial Sequence
<220> FEATURE:
<223> OTHER INFORMATION: synthetic oligonucleotide
```

```
<400> SEQUENCE: 2
ucaugaucga ugguguuac                                                19

<210> SEQ ID NO 3
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 3
gaauacagag auauggaau                                                19

<210> SEQ ID NO 4
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 4
auuccauauc ucuguauuc                                                19

<210> SEQ ID NO 5
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 5
cgaucaugau guagagugu                                                19

<210> SEQ ID NO 6
<211> LENGTH: 19
<212> TYPE: RNA
<213> ORGANISM: Artificial Sequence
<220> FEATURE:
<223> OTHER INFORMATION: synthetic oligonucleotide

<400> SEQUENCE: 6
acacucuaca ucaugaucg                                                19

<210> SEQ ID NO 7
<211> LENGTH: 15
<212> TYPE: RNA
<213> ORGANISM: Artificial Sequence
<220> FEATURE:
<223> OTHER INFORMATION: synthetic oligonucleotide

<400> SEQUENCE: 7
uagugcuccu gguug                                                    15

<210> SEQ ID NO 8
<211> LENGTH: 55
<212> TYPE: RNA
<213> ORGANISM: Artificial Sequence
<220> FEATURE:
<223> OTHER INFORMATION: synthetic oligonucleotide

<400> SEQUENCE: 8
guaacaccau cgaucaugau agugcuccug guugucauga ucgauggugu uacuu         55

<210> SEQ ID NO 9
<211> LENGTH: 21
```

```
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(19)
<223> OTHER INFORMATION: RNA

<400> SEQUENCE: 9
ggguguuuug gaggaguugt t                                                 21

<210> SEQ ID NO 10
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 10
aacaacuccu ccaaaacacc c                                                 21

<210> SEQ ID NO 11
<211> LENGTH: 55
<212> TYPE: RNA
<213> ORGANISM: Artificial Sequence
<220> FEATURE:
<223> OTHER INFORMATION: synthetic oligonucleotide

<400> SEQUENCE: 11
ucuuaaucgc guauaaggcu agugcuccug guuggccuua uacgcgauua agauu           55

<210> SEQ ID NO 12
<211> LENGTH: 55
<212> TYPE: RNA
<213> ORGANISM: Artificial Sequence
<220> FEATURE:
<223> OTHER INFORMATION: synthetic oligonucleotide

<400> SEQUENCE: 12
cuuacgcuga guacuucgau agugcuccug guugucgaag uacucagcgu aaguu           55
```